US009566174B1

(12) United States Patent
De Sapio et al.

(10) Patent No.: US 9,566,174 B1
(45) Date of Patent: Feb. 14, 2017

(54) SYSTEM FOR CONTROLLING BRAIN MACHINE INTERFACES AND NEURAL PROSTHETIC SYSTEMS

(71) Applicant: HRL Laboratories, LLC, Malibu, CA (US)

(72) Inventors: Vincent De Sapio, Westlake Village, CA (US); Narayan Srinivasa, Oak Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 20 days.

(21) Appl. No.: 14/540,835

(22) Filed: Nov. 13, 2014

Related U.S. Application Data

(60) Provisional application No. 61/903,538, filed on Nov. 13, 2013, provisional application No. 61/903,526, filed on Nov. 13, 2013.

(51) Int. Cl.
| | |
|---|---|
| *A61F 2/72* | (2006.01) |
| *A61F 2/68* | (2006.01) |
| *A61F 2/54* | (2006.01) |
| A61F 2/70 | (2006.01) |
| B25J 13/08 | (2006.01) |

(52) U.S. Cl.
CPC . *A61F 2/68* (2013.01); *A61F 2/54* (2013.01); *A61F 2/72* (2013.01); *A61F 2002/701* (2013.01); *A61F 2002/704* (2013.01); *B25J 13/087* (2013.01)

(58) Field of Classification Search
None
See application file for complete search history.

(56) References Cited

U.S. PATENT DOCUMENTS

| | | | | |
|---|---|---|---|---|
| 6,171,239 B1* | 1/2001 | Humphrey | ........... | A61B 5/0482 600/372 |
| 2010/0191079 A1* | 7/2010 | Shoureshi | ............ | A61B 5/0059 600/323 |

OTHER PUBLICATIONS

Anderson, F.C. and Pandy, M.G. (2001) 'Dynamic optimization of human walking', Journal of Biomechanical Engineering, vol. 123, No. 5, pp. 381-390.
Anderson, F.C. and Pandy, M.G. (2001) 'Static and dynamic optimization solutions for gait are practically equivalent', Journal of Biomechanics, vol. 34, No. 2, pp. 153-161.
Crowninshield, R.D. and Brand, R.A. (1981) 'A physiologically based criterion of muscle force prediction in locomotion', Journal of Biomechanics, vol. 14, No. 11, pp. 793-801.
(Continued)

*Primary Examiner* — David H Willse
(74) *Attorney, Agent, or Firm* — Tope-McKay & Associates

(57) ABSTRACT

Described is a system for controlling a torque controlled prosthetic device given motor intent inferred from neuroimaging data. The system includes at least one torque controlled prosthetic device operably connected with one or more processors. Further, the system is configured to receive neuroimaging data of a user from a neuroimaging device and decode the neuroimaging data to infer spatial motion intent of the user, where the spatial motion intent includes desired motion commands of the torque controlled prosthetic device represented in a coordinate system. The system thereafter executes, with a prosthesis controller, the motion commands as torque commands to cause the torque controlled prosthetic device to move according to the spatial motion intent of the user.

21 Claims, 18 Drawing Sheets

(56) References Cited

OTHER PUBLICATIONS

Davy, D.T. and Audu, M.L. (1987) 'A dynamic optimization technique for predicting muscle forces in the swing phase of gait', Journal of Biomechanics, vol. 20, No. 2, pp. 187-201.

De Sapio, V. (2011) 'Task-level control of motion and constraint forces in holonomically constrained robotic systems', in Proceedings of the 18th World Congress of the International Federation of Automatic Control, pp. 14622-14629.

De Sapio, V. and Park, J. (2010) 'Multitask constrained motion control using a mass-weighted orthogonal decomposition', Journal of Applied Mechanics, vol. 77, No. 4, pp. 041004-1 through 041004-10.

De Sapio, V., Khatib, O., and Delp, S. (2006) 'Task-level approaches for the control of constrained multibody systems', Multibody System Dynamics, vol. 16, No. 1, pp. 73-102.

De Sapio, V., Khatib, O. and Delp, S. (2005) 'Simulating the task-level control of human motion: a methodology and framework for implementation', The Visual Computer, vol. 21, No. 5, pp. 289-302.

Kaplan, M.L. and Heegaard, J.H. (2001) 'Predictive algorithms for neuromuscular control of human locomotion', Journal of Biomechanics, vol. 34, No. 8, pp. 1077-1083.

Khatib, O. (1995) 'Inertial properties in robotic manipulation: an object level framework', International Journal of Robotics Research, vol. 14, No. 1, pp. 19-36.

Khatib, O., Sentis, L., Park, J., and Warren, J. (2004) 'Whole-body dynamic behavior and control of human-like robots', International Journal of Humanoid Robotics, vol. 1, No. 1, pp. 29-43.

Siciliano, B., & Khatib, O. (Eds.). (2008). Chapter 6, Section 6.6, pp. 143-146, Springer Handbook of Robotics. Springer.

Neptune, R.R. (1999) 'Optimization algorithm performance in determining optimal controls in human movement analyses', Journal of Biomechanical Engineering, vol. 121, No. 2, pp. 249-252.

Sentis, L., Park, J. and Khatib, O. (2010) 'Compliant control of multicontact and center-of-mass behaviors in humanoid robots', IEEE Transactions on Robotics, vol. 26, No. 3, pp. 483-501.

Thelen, D.G. and Anderosn, F.C. (2006) 'Using computed muscle control to generate forward dynamic simulations of human walking from experimental data', Journal of Biomechanics,vol. 39, No. 6, pp. 1107-1115.

Thelen, D.G., Anderson, F.C. and Delp, S.L. (2003) 'Generating dynamic simulations of movement using computed muscle control', Journal of Biomechanics, vol. 36, No. 3, pp. 321-328.

Andersen, R. A., Hwang E. J., & Mulliken, G. H., (2010), Cognitive neural prosthetics, Annual review of psychology, 61, 169.

Bouganis, A., & Shanahan, M., (Jul. 2010), Training a spiking, neural network to control a 4-DoF robotic arm based on spike timing-dependent plasticity. In Neural Networks (IJCNN). The 2010 International Joint Conference on (pp. 1-8), IEEE.

Buneo, C. A., Jarvis, M. R., Batista: A. P., & Andersen, R. A., (2002), Direct visuomotor transformations for reaching. Nature, 416(6881), 632-636.

Davoodi, R., & Loeb, G. E., (Feb. 2011), MSMS software for VR simulations of neural prostheses and patient training and rehabilitation, In MMVR (pp. 156-162).

Davoodi, R., Urata, C., Hauschild, M., Khachani, M., & Loeb, G. E., (2007), Model-based development of neural prostheses for movement, Biomedical Engineering, IEEE Transactions on, 54(11), 1909-1918.

De Sapio, V., Khatib, O., & Delp, S., (2008), Least action principles and their application to constrained and task-level problems in robotics and biomechanics, Multibody System Dynamics, 19(3), 303-322.

Dethier, J., Nuyujukian, P., Eliasmith, C., Stewart, T. C., Elasaad, S. A., Shenoy, K. V., & Boahen, K. A., (2011), A brain-machine interface operating with a real-time spiking neural network control algorithm. In Advances in Neural Information Processing Systems (pp. 2213-2221).

Hauschild, M., Davoodi, R., & Loeb, G. E., (2007), A virtual reality environment for designing and fitting neural prosthetic limbs, Neural Systems and Rehabilitation Engineering, IEEE Transactions on, 15(1), 9-15.

Hochberg, L. R., Bacher. D., Jarosiewicz, B., Masse, N. Y., Simeral. J. D., Vogel, J., . . . & Donoghue, J. P., (2012), Reach and grasp by people with tetraplegia using a neurally controlled robotic arm, Nature, 485(7398), 372-375.

Khatib, O., (1995), Inertial properties in robotic manipulation: An object-level framework, The international Journal of Robotics Research, 14(1), 19-36.

Lebedev, M. A., Tate, A. J., Hanson, T. L., Li, Z., O'Doherty, J. E., Winans, J. A., . . . & Nicolelis, M. A., (2011), Future developments in brain-machine interface research. Clinics, 66, 25-32.

Naidu, D. S., Chen, C. H., Perez, A., & Schoen, M. P., (Aug. 2008), Control strategies for smart prosthetic hand technology: An overview, in Engineering in Medicine and Biology Society, EMBS 2008. 30th Annual International Conference of the IEEE (pp. 4314-4317), IEEE.

Sabes, P. N., (2000), The planning and control of reaching movements. Current opinion in neurobiology, 10(6), 740-746.

Srinivasa, N., &, Cho, Y., (2012), Self-organizing spiking neural model for learning fault-tolerant spatio-motor transformations, Neural Networks and Learning Systems. IEEE Transactions on, 23(10), 1526-1538.

Velliste, M., Perel, S., Spalding, M. C., Whitford, A. S., & Schwartz, A. B., (2008), Cortical control a prosthetic arm for self-feeding, Nature, 453(7198), 1098-1101.

De Sapio, V. (2011), Task-level control of motion and constraint forces in holonomically constrained robotic systems, in Proceedings of the 18th World Congress of the International Federation of Automatic Control.

De Sapio, V. and Park, J. (2010), Multitask constrained motion control using a mass-weighted orthogonal decomposition, Journal of Applied Mechanics, vol. 77, No. 4, p. 041004.

De Sapio, V., Khatib, O, and Delp, S. (2005), Simulating the task-level control of human motion: a methodology and framework for implementation, The Visual Computer, vol. 21, No. 5, pp. 289-302.

Thelen, D.G. and Anderson, F.C. (2006), Using computed muscle control to generate forward dynamic simulations of human walking from experimental data, Journal of Biomechanics,vol. 39, No. 6, p. 1107.

Thelen, D.G., Anderson, F.C. and Delp, S.L. (2003), Generating dynamic simulations of movement using computed muscle control, Journal of Biomechanics, vol. 36, No. 3, pp. 321-328.

De Sapio, V., Khatib. O., and Delp, S. (2006), Task-level approaches for the control of constrained multibody systems, Multibody System Dynamics, vol. 16, No. 1, pp. 73-102.

Bhattacharyya, R., Musallam, S., & Andersen, R. A. (2009). Parietal reach region encodes reach depth using retinal disparity and vergence angle signals. Journal of neurophysiology, 102(2), 805-816.

International Search Report of the International Searching, Authority for PCT/US2014/065537; date of mailing Mar. 31, 2015.

The Written Opinion of the International Searching Authority for PCT/US2014/065537; date of mailing Mar. 31, 2015.

Yanagisawa, T. et al., "Real-time control of a prosthetic hand using human electrocorticography signals: technical note," Journal of Neurosurgery, 2011, vol. 114, pp. 1715-1722.

De Sapio, V. et al., "Least action principles and their application to constrained and task-level problems in robotics and biomechanics," Multibody System Dynamics, 2008, vol. 19, pp. 303-322.

Dethier, J. et al., "A brain-machine interface operating with a realtime spiking neural network control algorithm." Advances in Neural Information Processing Systems, 2011, pp. 2213-2221.

Chestek, C. A. et al., "Neural prosthetic systems: current problems and future directions," 31st Annual International Conference of the IEEE EMBS, 2009, pp. 3369-3375.

Kim, H. K. et al., "Continuous shared control for stabilizing reaching and grasping with brain-machine interfaces," IEEE Transactions on Biomedical Engineering, 2006, vol. 53, pp. 1164-1173.

* cited by examiner

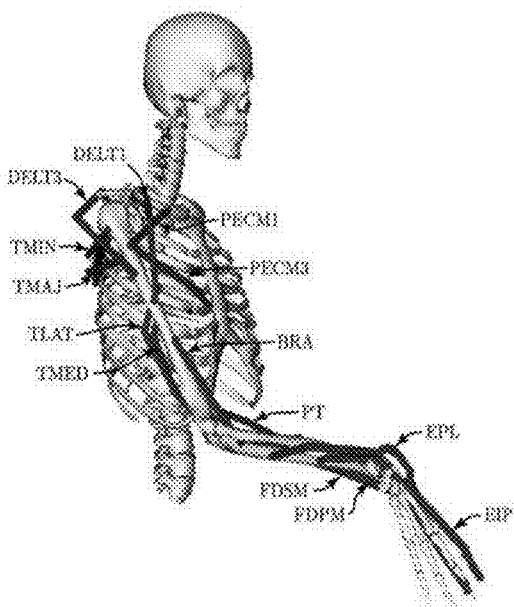
| Muscle | Span joint | $f_o$ (N) | $l_{M_o}$ (cm) |
|---|---|---|---|
| DELT1 | shoulder | 1142.60 | 9.76 |
| DELT3 | shoulder | 259.88 | 13.67 |
| TMAJ | shoulder | 425.39 | 16.24 |
| TMIN | shoulder | 354.25 | 7.41 |
| PECM1 | shoulder | 364.41 | 14.42 |
| PECM3 | shoulder | 390.55 | 13.85 |
| BRA | elbow | 987.26 | 8.58 |
| TLAT | elbow | 624.30 | 11.38 |
| TMED | elbow | 624.30 | 11.38 |
| PT | elbow | 566.22 | 4.92 |
| FDSM | wrist | 91.03 | 7.49 |
| FDPM | wrist | 81.65 | 8.35 |
| EPL | wrist | 39.46 | 5.40 |
| EIP | wrist | 21.70 | 5.89 |
FIG. 4A                    FIG. 4B

SYSTEM FOR CONTROLLING BRAIN MACHINE INTERFACES AND NEURAL PROSTHETIC SYSTEMS

GOVERNMENT RIGHTS

This invention was made with government support under U.S. Government Contract Number HR0011-09-C-0001. The Government has certain rights in the invention.

CROSS-REFERENCE TO RELATED APPLICATIONS

This is a non-provisional patent application of U.S. Provisional Application No. 61/903,538, filed Nov. 13, 2013, entitled, "A control and simulation architecture for application to brain machine interfaces and neural prosthetic systems."

This is ALSO a non-provisional patent application of U.S. Provisional Application No. 61/903,526, filed Nov. 13, 2013, entitled, "A goal-oriented sensorimotor controller for controlling musculoskeletal simulations with neural excitation commands."

BACKGROUND OF THE INVENTION (1) Field of Invention

The present invention relates to a robotic control system and, more particularly, to a system for controlling robotic prosthetic devices given motor intent inferred from neuroimaging data.

(2) Description of Related Art

Brain machine interfaces (BMI) and neural prosthetics offer great hope for restoring function to people with spinal cord injuries and amputees, as well augmenting and enhancing the abilities of people with full motor function. There have been a number of advances in neural imaging as well as in decoding motor intent from neuroimaging data. However, with regard to prosthetic device control there have been fewer advances, with most approaches rooted in conventional robotic control.

There is a body of work in BMI and neural prosthetics research which addresses the decoding of cortical signals for the downstream execution of motion commands by an external device (see, for example, the List of Incorporated Literature References, Literature Reference Nos. 1, 9, 11, 12, and 15). Most of this work focuses on the neural decoding with less rigor applied to the prosthesis control. In cases where a robotic arm prosthesis is controlled, the motion trajectory is typically converted into joint commands and executed using joint space control (see, for example, Literature Reference Nos. 11, 12, and 15).

To date, no known prosthetic control system has been proposed which uses a task/posture decomposition. Task/posture decomposition has particular advantages over joint space control in BMIs. It is based on an abstraction analogous to the manner in which cortical signals are encoded (e.g., eye-centered, hand-centered Cartesian coordinates). Further, it is generalizable to whole body prosthetic control involving multiple prosthetic limbs and high degree-of-freedom kinematics. Joint space prosthetic control is limited in this capacity due to its reliance on inverse kinematics solutions. Additionally, task/posture decomposition allows for the specification of postural behaviors based on minimizing important objective functions (e.g. power consumption, virtual muscle effort, etc.) consistent with the execution of cortical motion commands.

There has been some work on applying neuromorphic computing architectures to BMIs and neural prosthetic systems. For example, the work of Dethier et al. focused on the use of artificial spiking neural networks for decoding and filtering cortical signals (Kalman filter based decoding using endpoint kinematics as the state vector and neural spike rates as the measurement vector) rather than prosthetic control (see Literature Reference No. 7).

Additionally, the work of Bouganis and Shanahan was directed to controlling a robotic arm using artificial spiking neural networks; although their work was not applied to a neural prosthetic system (see Literature Reference No. 2).

Other researchers performed work in the simulation of neural prosthetic limbs in conjunction with biomechanical models (see Literature Reference Nos. 4, 5, and 8). However, while their work implements musculoskeletal models into the simulation, the focus of these efforts is on simulating and validating the control of the prosthetic device. Thus, again, there is no known system that integrates a sensorimotor controller, in addition to the prosthetic controller.

Therefore, a continuing need exists for a system that allows enhanced modeling and analysis of the interface issues associated, not just with the biological and engineered components, but also with the biological and engineered control systems. Further, a need exists for a system-level architecture for applying artificial spiking neural networks to the learning of motor maps, consistent with postural criteria, for controlling motion in BMI and neural prosthetic systems.

SUMMARY OF INVENTION

Described is a system for controlling a torque controlled prosthetic device given motor intent inferred from neuroimaging data. The system includes one or more processors and a memory, the memory having executable instructions encoded thereon, such that upon execution of the instructions, the one or more processors perform several operations, such as receiving neuroimaging data of a user from a neuroimaging device. The neuroimaging data is then decoded to infer spatial motion intent of the user, where the spatial motion intent includes desired motion commands of the torque controlled prosthetic device represented in a coordinate system. Thereafter, the system executes, with a prosthesis controller, the motion commands as torque commands to cause the torque controlled prosthetic device to move according to the spatial motion intent of the user.

In another aspect, the system includes at least one torque controlled prosthetic device operably connected with the one or more processors.

In yet another aspect, the system performs an operation of receiving, in the controller, sensory information regarding a current state of the prosthetic device.

Additionally, in executing the motion commands, the motion commands are executed using a task decomposition and posture decomposition, wherein the task decomposition is a task space control and the posture decomposition is formulated as a cost potential which represents a cost function.

Further, in executing the motion commands, the motion commands are executed as torque commands that generate a desired task space control while minimizing the cost potential.

In yet another aspect, in executing the motion commands, the motion commands are executing using a spiking neural network.

In another aspect, the prosthesis controller is a neuromorphic prosthesis controller and further comprises: a neuromorphic spike encoder to represent the motion command as a set of neural spikes; a neuromorphic motor mapper to map the neural spikes representing Cartesian displacements to neural spikes representing configuration (joint) space displacements; a spike decoder to decode the neural spikes representing configuration (joint) space displacements and generate a joint space command; and a joint servo to execute the joint space command.

In yet another aspect, the system performs operations of receiving a model of the prosthetic device and a musculoskeletal model of the user, wherein the musculoskeletal model includes musculoskeletal dynamics that include steady state tendon forces; generating, with a sensorimotor controller, simulated neural excitations given the motion commands to drive a set of muscle activations in a musculoskeletal simulation; and generating, with the prosthesis controller, simulated actuator joint torques given the motion commands to drive a simulated prosthetic device.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 4A is a simplified model of a human arm actuated by 14 muscles;

FIG. 4B is a table illustrating corresponding maximum isometric forces, $f_o$, and optimal fiber lengths, $l_{M_0}$ of the muscles illustrated in FIG. 4A;

DETAILED DESCRIPTION

Figure 1:
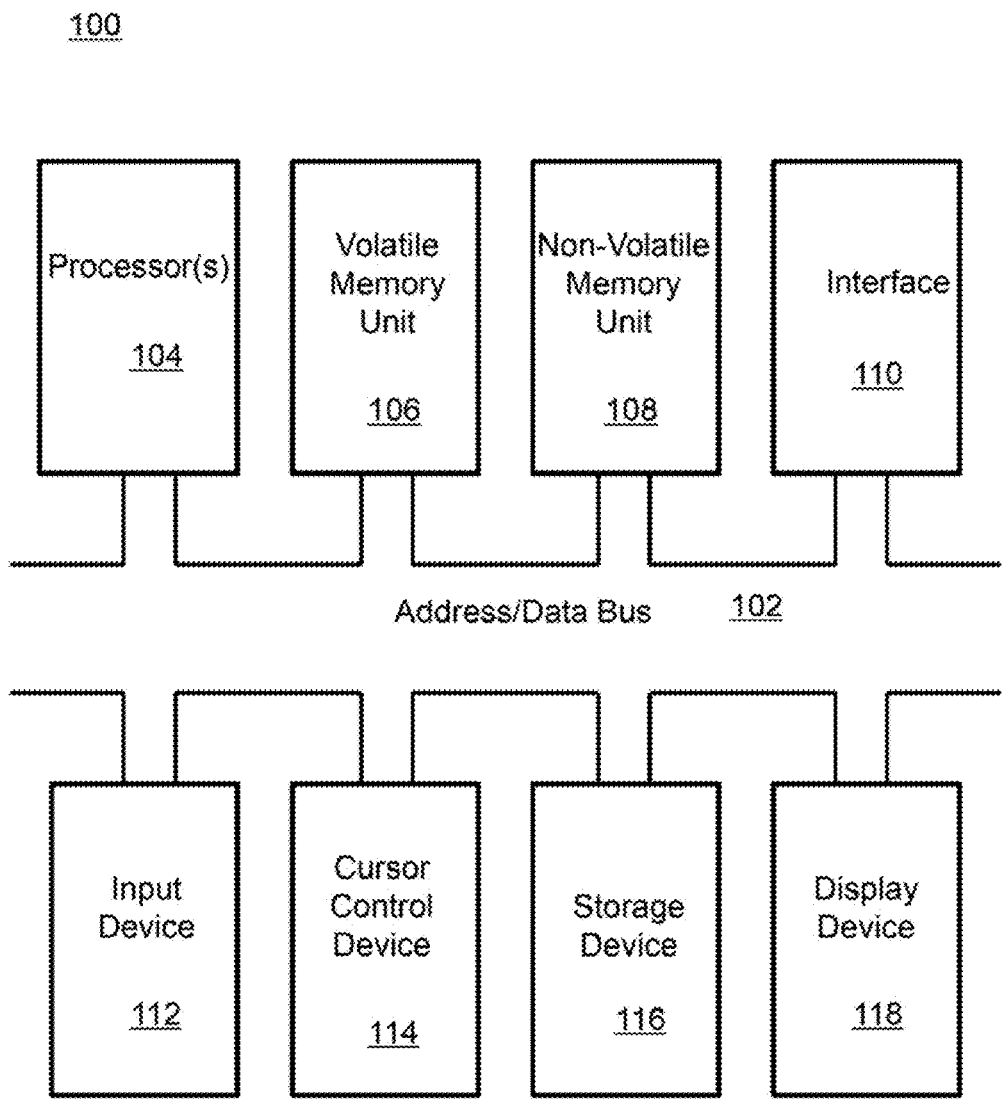
FIG. 1 is a block diagram depicting the components of system according to the principles of the present invention.

The present invention relates to a robotic control system and, more particularly, to a system for controlling robotic prosthetic devices given motor intent inferred from neuroimaging data. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of incorporated literature references is provided. Next, a description of various principal aspects of the present invention is provided. Subsequently, an introduction provides the reader with a general understanding of the present invention. Finally, details of the present invention are provided to give an understanding of the specific aspects.

(1) LIST OF INCORPORATED LITERATURE REFERENCES

The following references are cited throughout this application. For clarity and convenience, the references are listed herein as a central resource for the reader. The following references are hereby incorporated by reference as though fully included herein. The references are cited in the application by referring to the corresponding literature reference number.

1. Andersen, R. A., Hwang, E. J., & Mulliken, G. H., (2010), Cognitive neural prosthetics, Annual review of psychology, 61, 169.
2. Bouganis, A., & Shanahan, M., (2010, July), Training a spiking neural network to control a 4-DoF robotic arm based on spike timing-dependent plasticity. In Neural Networks (IJCNN), The 2010 International Joint Conference on (pp. 1-8), IEEE.
3. Buneo, C. A., Jarvis, M. R., Batista, A. P., & Andersen, R. A., (2002), Direct visuomotor transformations for reaching. Nature, 416(6881), 632-636.
4. Davoodi, R., & Loeb, G. E., (2011, February), MSMS software for VR simulations of neural prostheses and patient training and rehabilitation, In MMVR (pp. 156-162).
5. Davoodi, R., Urata, C., Hauschild, M., Khachani, M., & Loeb, G. E., (2007), Model-based development of neural prostheses for movement, Biomedical Engineering, IEEE Transactions on, 54(11), 1909-1918.
6. De Sapio, V., Khatib, O., & Delp, S., (2008), Least action principles and their application to constrained and task-level problems in robotics and biomechanics, Multibody System Dynamics, 19(3), 303-322.
7. Dethier, J., Nuyujukian, P., Eliasmith, C., Stewart, T. C., Elasaad, S. A., Shenoy, K. V., & Boahen, K. A., (2011), A brain-machine interface operating with a real-time spiking neural network control algorithm. In Advances in Neural Information Processing Systems (pp. 2213-2221).
8. Hauschild, M., Davoodi, R., & Loeb, G. E., (2007), A virtual reality environment for designing and fitting neural prosthetic limbs, Neural Systems and Rehabilitation Engineering, IEEE Transactions on, 15(1), 9-15.
9. Hochberg, L. R., Bacher, D., Jarosiewicz, B., Masse, N. Y., Simeral, J. D., Vogel, J., . . . & Donoghue, J. P., (2012), Reach and grasp by people with tetraplegia using a neurally controlled robotic arm, Nature, 485(7398), 372-375.
10. Khatib, O., (1995), Inertial properties in robotic manipulation: An object-level framework, The International Journal of Robotics Research, 14(1), 19-36.
11. Lebedev, M. A., Tate, A. J., Hanson, T. L., Li, Z., O'Doherty, J. E., Winans, J. A., . . . & Nicolelis, M. A., (2011), Future developments in brain-machine interface research. Clinics, 66, 25-32.
12. Naidu, D. S., Chen, C. H., Perez, A., & Schoen, M. P., (2008, August), Control strategies for smart prosthetic hand technology: An overview, In Engineering in Medicine and Biology Society, EMBS 2008. 30th Annual International Conference of the IEEE (pp. 4314-4317), IEEE.
13. Sabes, P. N., (2000), The planning and control of reaching movements. Current opinion in neurobiology, 10(6), 740-746.
14. Srinivasa, N., & Cho, Y., (2012), Self-organizing spiking neural model for learning fault-tolerant spatio-motor transformations, Neural Networks and Learning Systems, IEEE Transactions on, 23(10), 1526-1538.
15. Velliste, M., Perel, S., Spalding, M. C., Whitford, A. S., & Schwartz, A. B., (2008), Conical control of a prosthetic arm for self-feeding, Nature, 453(7198), 1098-1101.
16. De Sapio, V. (2011), Task-level control of motion and constraint forces in holonomically constrained robotic systems, in Proceedings of the 18th World Congress of the International Federation of Automatic Control.
17. De Sapio, V. and Park, J. (2010), Multitask constrained motion control using a mass-weighted orthogonal decomposition, Journal of Applied Mechanics, Vol. 77, No. 4, p. 041004.
18. De Sapio, V., Khatib, O. and Delp, S. (2005), Simulating the task-level control of human motion: a methodology and framework for implementation, The Visual Computer, Vol. 21, No. 5, pp. 289-302.
19. Thelen, D. G. and Anderson, F. C. (2006), Using computed muscle control to generate forward dynamic simulations of human walking from experimental data, Journal of Biomechanics, Vol. 39, No. 6, p. 1107.
20. Thelen, D. G., Anderson, F. C. and Delp, S. L. (2003), Generating dynamic simulations of movement using computed muscle control, Journal of Biomechanics, Vol. 36, No. 3, pp. 321-328.
21. De Sapio, V., Khatib, O., and Delp, S. (2006), Task-level approaches for the control of constrained multibody systems, Multibody System Dynamics, Vol. 16, No. 1, pp. 73-102.

(2) Principal Aspects

The present invention has three "principal" aspects. The first is a system for controlling robotic prosthetic devices given motor intent inferred from neuroimaging data. The system is typically in the form of a computer system operating software or in the form of a "hard-coded" instruction set. This system may be incorporated into a wide variety of devices that provide different functionalities. In one aspect, the system is incorporated into a robot having actuators and appendages or other motion operable components and any other components as may be required to provide the functionality as described herein. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
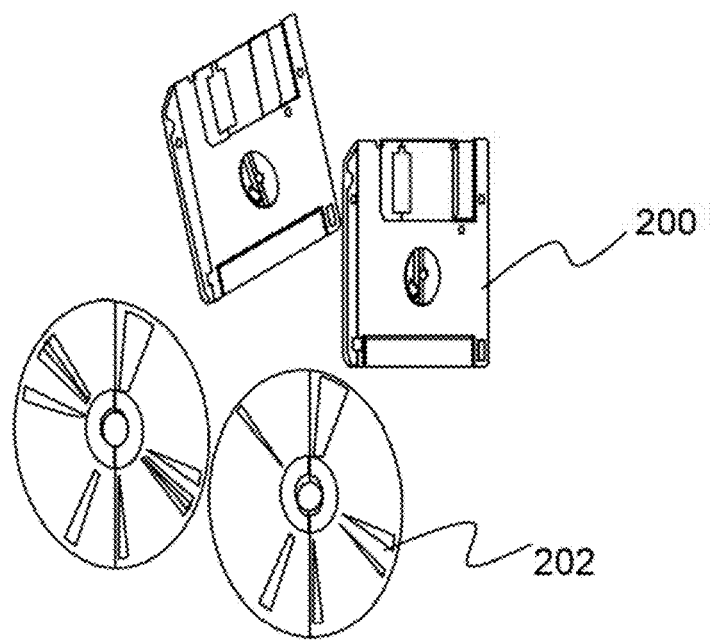
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

Brain machine interfaces (BMI) and neural prosthetics offer great hope for restoring function to people with spinal cord injuries and amputees, as well augmenting and enhancing the abilities of people with full motor function. There have been a number of advances in neural imaging as well as in decoding motor intent from neuroimaging data. However, with regard to prosthetic device control there have been fewer advances, with most approaches rooted in conventional robotic control.

Thus, the system described herein provides a system-level architecture for controlling robotic prosthetic devices given motor intent inferred from neuroimaging data. The system also provides a simulation architecture to facilitate virtual testing of the specific controller and prosthetic device design, with respect to the human subject, prior to any clinical intervention. Two unique control architectures will be described. One controller is based on a bio-inspired task/posture decomposition of motion intended for implementation on conventional digital computing hardware. The other controller is based on a neuromorphic mapping of task motion to joint motion with a bio-inspired resolution of kinematic redundancy, which can be implemented on neuromorphic computing hardware. A unique aspect is that both approaches utilize bio-inspired abstractions for controlling prosthetic devices in a natural human-like manner rather than utilizing conventional inverse kinematic approaches. Specific instantiations of either of these control architectures can be tested with a human-in-the-loop using a novel model-based simulation environment. In this environment actual cortical output from neuroimaging equipment (electroencephalography (EEG), functional magnetic resonance imaging (fMRI), etc.) attached to the subject will drive both a biomechanical model of the subject and a model of the prosthetic device to be tested. This modeling provides a technique for testing the efficacy of the prosthetic device, the controller, and the overall bio-integration of the prosthetic hardware with the subject, without requiring the subject to be physically coupled with the actual prosthetic hardware.

The ability of the simulation environment to drive both the motion of the prosthetic device and the motion of the simulated subject through cortical commands (i.e., BMI) is unique and can be utilized by a variety of prosthetic manufacturers and/or developers. For example, human augmentation technologies can be implemented for enhancing the capabilities of the manufacturing floor worker. These technologies include assistive exoskeletons and other devices to increase worker productivity and reduce injury. The invention offers significant capabilities for the development of next generation BMIs, such as user performance enhancement, assistive robotic devices, and neural prosthetic technologies.

(4) Specific Details

Described are two control architectures for controlling robotic prosthetic devices given motor intent inferred from neuroimaging data. Additionally, a simulation architecture is described for human-in-the-loop virtual testing of bio-integration issues associated with the prosthetic hardware. Both control architectures start with the assumption of a source of decoded cortical data from the brain which represents high-level motor intent. This motor intent is in the form of desired motion commands represented in different Cartesian coordinate systems (eye-centered, hand-centered, etc.) using visumotor transformations. Examples of such visumotor transformations were described in Literature Reference Nos. 3 and 13. This desired motion command is referred to herein as $x_d$, a multidimensional vector of task coordinates (e.g. Cartesian coordinates associated motion of a single hand or coordinated motion of both hands). The goal is to control the prosthetic device based on this motor intent.

Before describing the first control architecture based on bio-inspired task/posture decomposition of motion, it is necessary to define the dynamics of the prosthetic device. In joint space, the dynamics are defined as follows:

$$\tau = M(q)\ddot{q} + b(q,\dot{q}) + g(q),$$

where q is the vector of joint coordinates, $\tau$, is the vector of applied joint torques, M(q), is the joint space mass matrix, $b(q,\dot{q})$, is the vector of centrifugal and Coriolis forces, and g(q) is the vector of gravity forces. Inverse kinematics is conventionally used to map a desired Cartesian goal into a set of joint angles, $\{x^{-1}(q)|x \rightarrow q\}$. Subsequently, given the joint level commands the prosthetic device is controlled by serving individual joints or by using computed torque control. Given an anthropomorphic prosthetic device designed to replace a human limb (e.g., the human arm), it is necessary to address kinematic redundancy in the limb motion. That is, the device will typically possess more joint coordinates than are required by the motion command. From a robotic control perspective this implies that there are an infinite number of joint coordinate solutions associated with a given motion command.

The approach to dealing with this issue is to represent the dynamics of the prosthetic device in task space, a more natural space for addressing the control problem since the decoded cortical motion command is expressed in this space. A task space representation of the dynamics is given by, $$f = \Lambda(q)\ddot{x} + \mu(q,\dot{q}) + p(q),$$

where x is a description of task coordinates that are to be controlled, f, are the control forces that act at the task, and $\Lambda(q)$, $\mu(q,\dot{q})$, and p(q), are the task space mass matrix, centrifugal and Coriolis force vector, and gravity force vector, respectively. Task space was described by Khatib in Literature Reference No. 10.

The applied joint torques are given by, $$\tau = J^T f + N^T \tau_p,$$

where J is the Jacobian of the task coordinates, $N^T$ is the null space projection matrix, and $\tau_p$ is an arbitrary joint torque filtered through the null space projection matrix. The key point to note here is that control of the prosthetic device can be decomposed into a task-level component and a complementary postural component (due to the kinematic redundancy). Based on the choice of a particular generalized inverse of the Jacobian these two components of motion control are guaranteed to be dynamically consistent with each other and, as such, control can be synthesized to execute the cortical motion command while simultaneously achieving some postural objective for the prosthetic device. This postural objective can be based on minimizing some physiological cost criterion or it can be based on minimizing a power consumption criterion for the device. In the former case, while the prosthetic device is not necessarily actuated in a manner analogous to the biological appendage it is replacing, encoding a physiological criterion into its control can result in more human-like behavior of the device's postural motion. This would achieve the desirable effect of the device moving more consistently with how the subject's own appendage would move.

Figure 3:
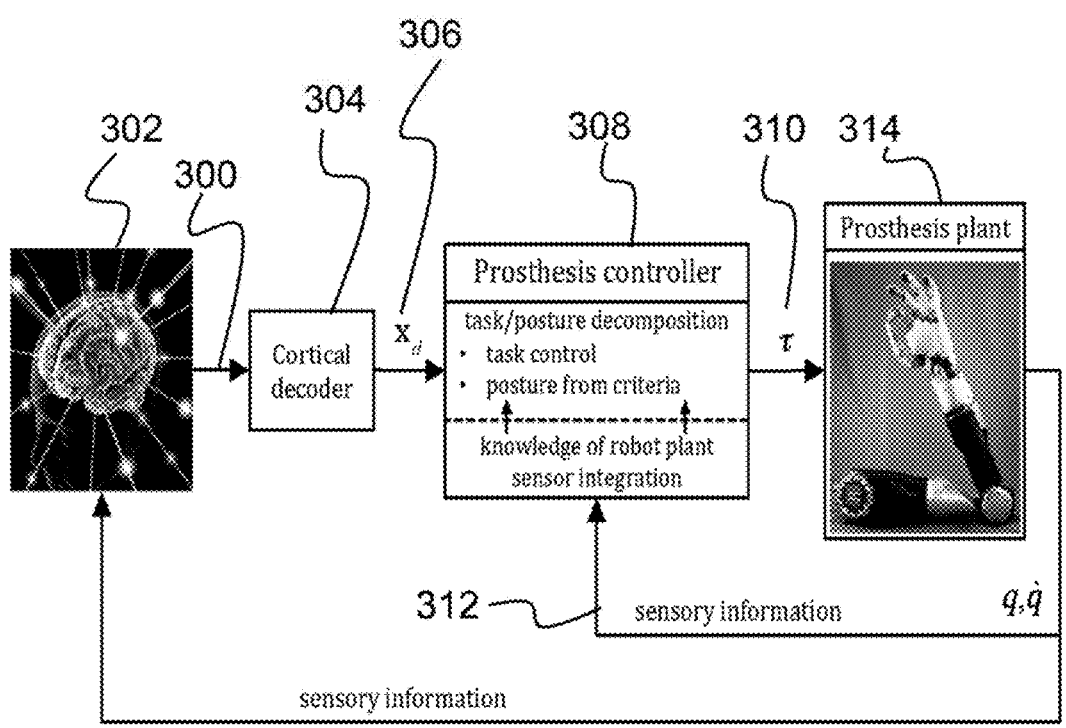
FIG. 3 is a process flow-chart illustrating how high-level motor intent from the brain is decoded and a task-level motion command is transmitted to the prosthetic device controller, which in turn executes the motion command using a task/posture decomposition.

For further understanding, FIG. 3 depicts the system-level architecture associated with this approach. High-level motor intent from the brain 302 is decoded (with a cortical decoder 304) and a task-level motion command 306 is transmitted to the prosthetic device controller 308. High-level motor intent is captured using a neuroimaging device or any other suitable device operable for capturing neuroimaging data 300, non-limiting examples of which include neuroimaging equipment such as electroencephalography (EEG), and functional magnetic resonance imaging (fMRI). The cortical decoder 304 uses a decoding algorithm to infer spatial motion intent 306 from the neuroimaging data 300. As an example and as noted above, this motor intent is in the form of desired motion commands represented in different Cartesian coordinate systems (eye-centered, hand-centered, etc.) using visumotor transformations.

The controller 308 executes the motion command using a task/posture decomposition. Relevant physiological criteria (i.e., postural criterion) or device power consumption criteria can be used to drive the postural component of motion 310, consistent with the cortical command. Sensory information 312 (e.g., joint angles of the current state of the prosthetic device 314) from the prosthetic device 314 is fed back to the controller 308, resulting in closed loop control. The architecture also accommodates sensory information 312 from the prosthetic device 314 being sent to the brain 302 to facilitate afferent proprioception.

In formulating a postural criterion, a potential, $U(q)$, can be specified as representing some cost function. An example of suitable cost functions was described by De Sapio in Literature Reference No. 6. The task-level motion command can be controlled while simultaneously controlling motion in the complementary posture space to minimize $U(q)$. This can be accomplished by applying gradient descent in the null/posture space. That is, $$-N^T \frac{\partial U}{\partial q}.$$

The task space control equations can then be expressed as follows:

$$f = \hat{\Lambda} f^* + \hat{\mu} + \hat{p},$$

where $\hat{\cdot}$ represents estimates of the dynamic parameters and $f^*$ is the control law. A proportional-derivative (PD) control law can be expressed as:

$$f^* = K_p(x_d - x) + K_v(\dot{x}_d - \dot{x}) + \ddot{x}_d,$$

where $K_p$ and $K_v$ are control gains. The control torque, which generates the desired task space control while minimizing the instantaneous cost potential in the posture space, is then, $$\tau = J^T f - \hat{N}^T \frac{\partial U}{\partial q}.$$

A physiological cost criterion, like muscle effort, can be selectively represented. For example, De Sapio, et al., (see Literature Reference No. 6), proposed the following muscle effort criterion related to minimizing muscle activation, $$U = g^T [R(K_f K_f^T) R^T]^{-1} g,$$

where $g(q)$ is the gravity torque, $R(q)$ is the matrix of muscle moment arms, and $K_f(q)$ is the diagonal matrix mapping muscle activation, a, to muscle force, f. The elements of $K_f$ for a given muscle can be modeled by, $$f_o e^{-s\left(\frac{l(q)}{l_{M_o}} - 1\right)^2},$$

where $l(q)$ is the muscle length, and $f_o$ and $l_{M_o}$ represent the maximum isometric muscle force and the optimal muscle fiber length respectively.

This effort criterion can be used to design an arm prosthesis controller based on the architecture of FIG. 3. For illustrative purposes and as a non-limiting example, the characteristics of the biomechanical model of FIG. 4A are employed into an arm prosthesis controller. FIG. 4A illustrates a simplified biomechanical model of the human arm actuated by 14 muscles, while FIG. 4B is a table illustrating the maximum isometric forces, $f_o$, and optimal fiber lengths, $l_{M_o}$ for the biomechanical model of FIG. 4A. The control law is defined as, $$f^* = k_p(x_d - x) - k_v \dot{x},$$

and the control torque is defined as, $$\tau = J^T f^* + \hat{g} - \hat{N}^T \left(k_e \frac{\partial U}{\partial q} + k_d \dot{q}\right),$$

where a dissipative term, $k_d \dot{q}$, and a gain, $k_e$, are added on the gradient descent term in the posture space portion of the control torque.

Figure 5A:
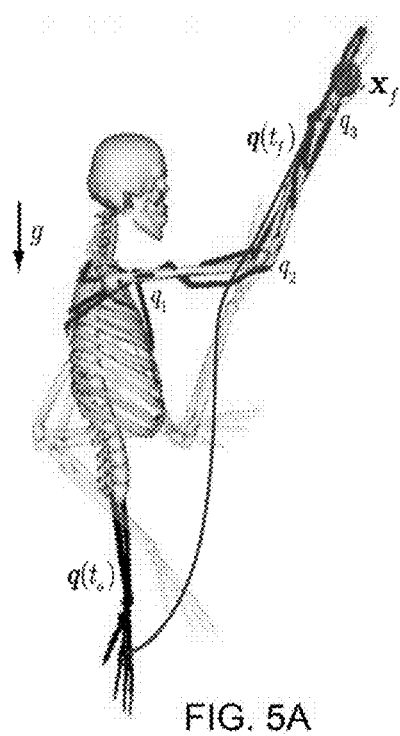
FIG. 5A is an illustration of a redundant muscle-actuated model of the human arm used as a physiological template for controlling a prosthetic arm.
Figure 5B:
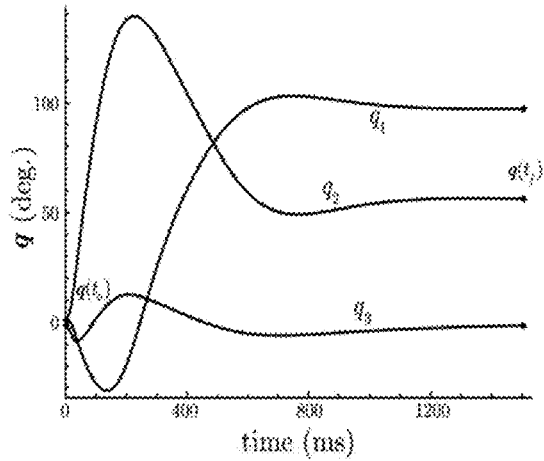
FIG. 5B is a graph illustrating time histories of joint motion while performing a simulation run of the model as illustrated in FIG. 5A.
Figure 5C:
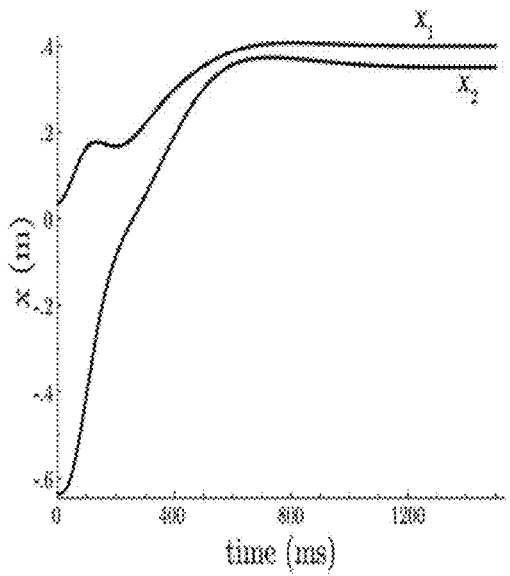
FIG. 5C is a graph illustrating time histories of hand motion while performing a simulation run of the model as illustrated in FIG. 5A.
Figure 5D:
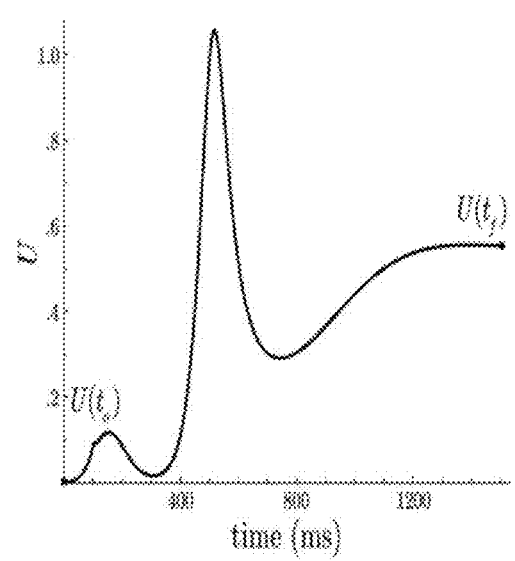
FIG. 5D is a graph illustrating time histories of muscle effort while performing a simulation run of the model as illustrated in FIG. 5A.

FIG. 5A illustrates a redundant muscle-actuated model of the human arm used as a physiological template for controlling a prosthetic arm, while FIGS. 5B, 5C and 5D are graphs illustrating time histories of joint motion, hand motion, and muscle effort, respectively, for a simulation run using the model of FIG. 5A. The model of FIG. 5A depicts initial and final configurations (joint angles), $q(t_o)$ and $q(t_f)$, associated with gradient descent movement to a target, $x_f$. The motion corresponds to gradient descent of the muscle effort, subject to the task requirement. The posture control seeks to reduce the muscle effort but is also constrained by the task requirement.

The controller achieves the final target objective while the posture control simultaneously seeks to reduce the muscle effort (consistent with the task requirement). No compensation for the dynamics (except for gravity) was included in the control. Thus, there is no feedback linearization of the inertial terms present in the control. Normally, perfect feedback linearization would produce straight line motion to the goal. In the absence of feedback, linearization non-straight line motion results.

It is noted that the biomechanical model of FIG. 4A is used to generate a physiological criterion that is encoded in the prosthesis controller. The actuation system of the prosthetic arm need not be analogous to its biological muscle-driven counterpart. Rather, the biological muscle model defines a set of virtual muscles that direct the postural control of the prosthetic device in a bio-inspired manner, even if conventional robot actuators (e.g., DC motors, etc.) are used in the prosthetic device to control joint movements.

The control architecture depicted in FIG. 3 is intended to be implemented on conventional digital computing hardware and integrate with a prosthetic device if desired. An approach that would implement neuromorphic hardware is also described below. This involves the design of an artificial spiking neural network to learn the mapping between task-level motion commands, derived from decoded cortical signals, and joint space commands. In the approach described above, kinematic redundancy in the prosthetic device was resolved using a task/posture decomposition. In the case of motor map learning by an artificial spiking neural network, kinematic redundancy also needs to be addressed since a differential movement in x would result in an infinite space of differential movements in q.

Figure 6A:
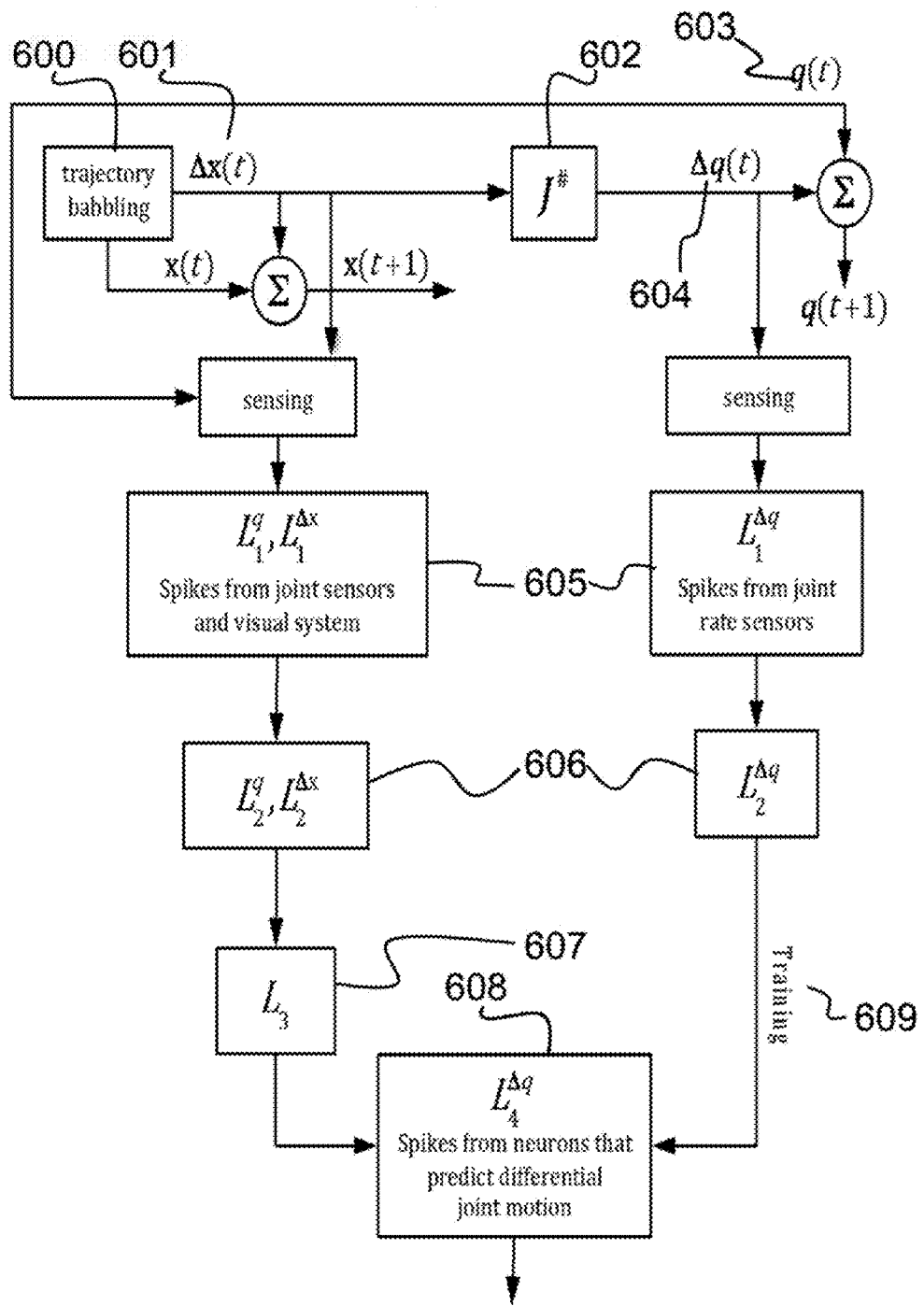
FIG. 6A is a flow chart illustrating an artificial spiking neural network where motor map redundancy is resolved by training the network only on unique solutions of the inverse mapping given by $\Delta q = J\# \Delta x$.
Figure 6B:
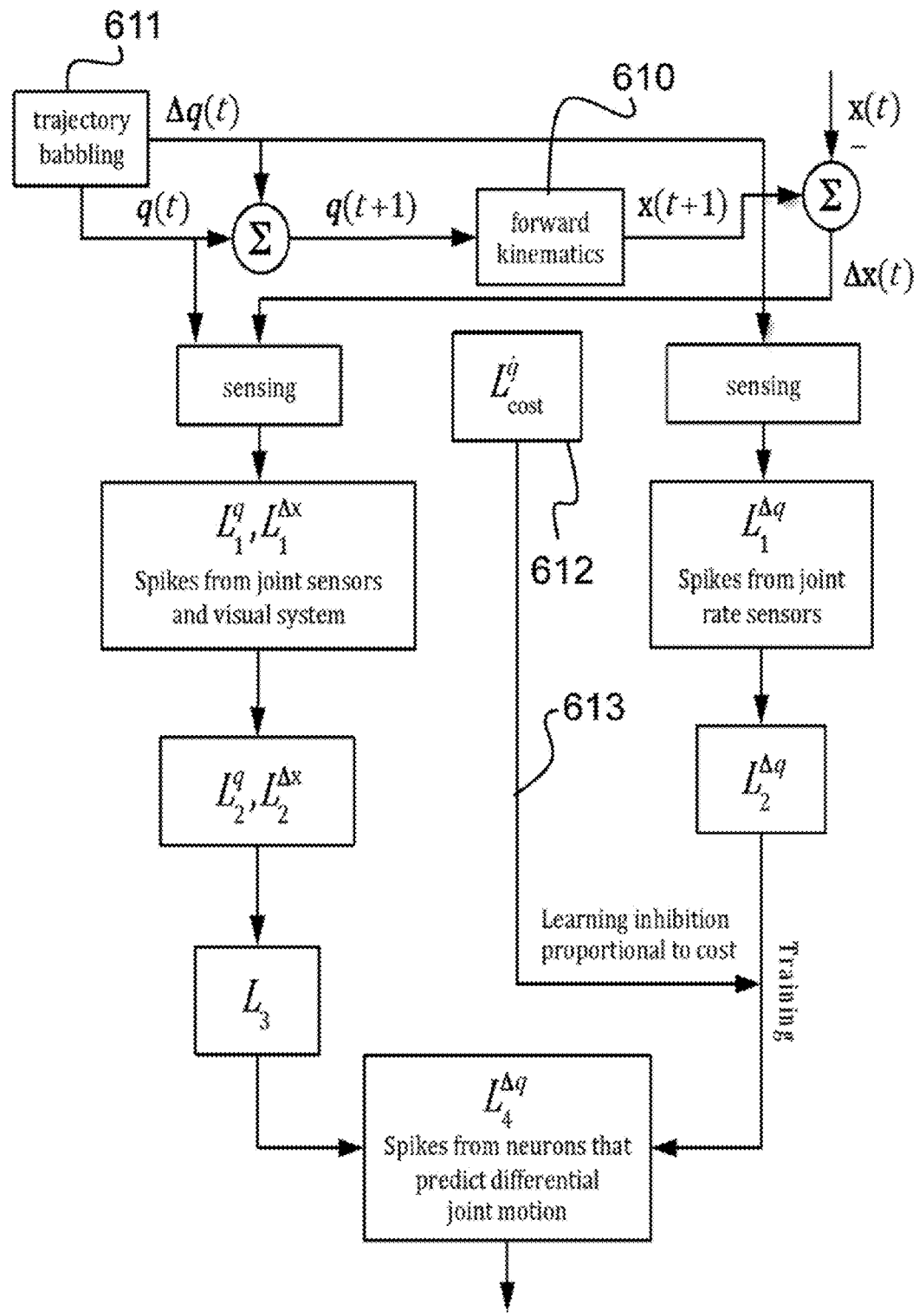
FIG. 6B is a flow chart illustrating an artificial spiking neural network where motor map redundancy is resolved by explicitly inhibiting the learning of solutions where the cost is high.

FIGS. 6A and 6B depict artificial spiking neural networks with two different approaches for resolving kinematic redundancy. Both networks learn the inverse kinematic mapping using trajectory babbling 600, 611 of the prosthetic arm. Kinematic redundancy impacts the training such that for a given configuration (set of joint angles), q 603, and Cartesian displacement, $\Delta x$ 601, there will be multiple values of configuration (joint) space displacement, $\Delta q$ 604 to learn. In other words, the forward mapping, $\Delta x = J(q)\Delta q$, cannot be uniquely inverted. As shown in FIG. 6A, this can be resolved by using a specific generalized inverse of J (i.e., J# 602), such that $\Delta q = J\# \Delta x$. Given this unique mapping, the spiking neural network of FIG. 6A trains on the output of the trajectory babbling in Cartesian space 600. The signals q 603 and $\Delta x$ 601 serve as the context for the training and the signal $\Delta q$ 604 serves as the signal to be learned with respect to that context. Signal 603 represents the current joint angle configuration that is being sensed at any given time.

The spikes representing these signals act as inputs to layer 1 605 of spiking neurons. The outputs of layer 1 605 act as spike inputs to layer 2 606. An additional layer 3 607 of neurons is employed on the context side (q 603 and $\Delta x$ 601 input side). In this layer each neuron codes for a single combined representation of both the configuration, q 603, and Cartesian displacement, $\Delta x$ (see Literature Reference No. 14). In layer 4 608 the synaptic weights of the spiking neurons in that layer are reinforced consistent with learning the training signals 609. Spike timing-dependent plasticity (see Literature Reference Nos. 2 and 14) is utilized to modulate the synaptic weights in the layers. After sufficient training on motor babbling data the spike timing-dependent plasticity can be turned off as the neurons in layer 4 607 will have learned the differential kinematic mapping. Note that x(t+1) and q(t+1) denote a new value for a next time step.

The generalized inverse, J# 602, can be chosen based on the minimization of some quadratic form. For example, to find a solution that minimizes $\|\dot{q}\|^2$, the following solution can be used:

$$\Delta q = J^+ \Delta x = J^T (JJ^T)^{-1} \Delta x.$$

As another example, a solution that minimizes the instantaneous kinetic energy of the system, $\dot{q}^T M \dot{q}/2$, would be given by, $$\Delta q = \bar{J}\Delta x = M^{-1} J^T (JM^{-1} = J^T)^{-1} \Delta x.$$

Alternatively, a solution that minimizes the instantaneous muscle fiber displacement rate, $\|\dot{l}\|^2 = \dot{q}^T RR^T \dot{q}$, would be given by, $$\Delta q = (RR^T)^{-1} J^T [(J(RR^T)^{-1} J^T]^{-1} \Delta x.$$

As shown in FIG. 6B, the redundancy problem can also be resolved by adding a layer of neurons 612 that explicitly inhibits the learning of solutions where the cost (physiological or otherwise) is high. The structure of FIG. 6B is similar to FIG. 6A. However, rather than using a generalized inverse to compute a unique value of $\Delta q$ to learn for a given configuration, q, and Cartesian displacement, $\Delta x$, forward kinematics 610 is used to compute the unique forward mapping from the configuration (joint) space motor babbling 611 to Cartesian space. While many values of $\Delta q$ will satisfy this mapping for a given value of q and $\Delta x$, a layer of neurons 612 is incorporated to inhibit the learning 613 of $\Delta q$ signals with high cost values. In this way training will be directed at learning $\Delta q$ values associated with minimal cost values.

Referring again to FIGS. 6A and 6B, the spiking neural networks operate as neuromorphic motor mappers (illustrated as element 708 in FIG. 7) that map Cartesian displacement, $\Delta x$ 601, to configuration (joint) space displacement, $\Delta q$. Utilizing this neuromorphic motor mapper 708 a feedback loop 700 is specified in FIG. 7 to control the prosthetic arm. The overall system consists of output from a cortical decoder, which specifies intentional movement 306 of the arm in Cartesian space. This signal is encoded as spikes 706 by the neuromorphic spike encoder 702. These spikes, as well as joint angle measurements from the prosthetic arm 714 encoded as spikes 720, act as input to the neuromorphic motor mapper 708. A spiking output representing the learned mapping to the configuration (joint) space displacement, $\Delta q$, is decoded 710 and sent to a joint servo 712, which controls the motion of the prosthetic arm 718.

Figure 7:
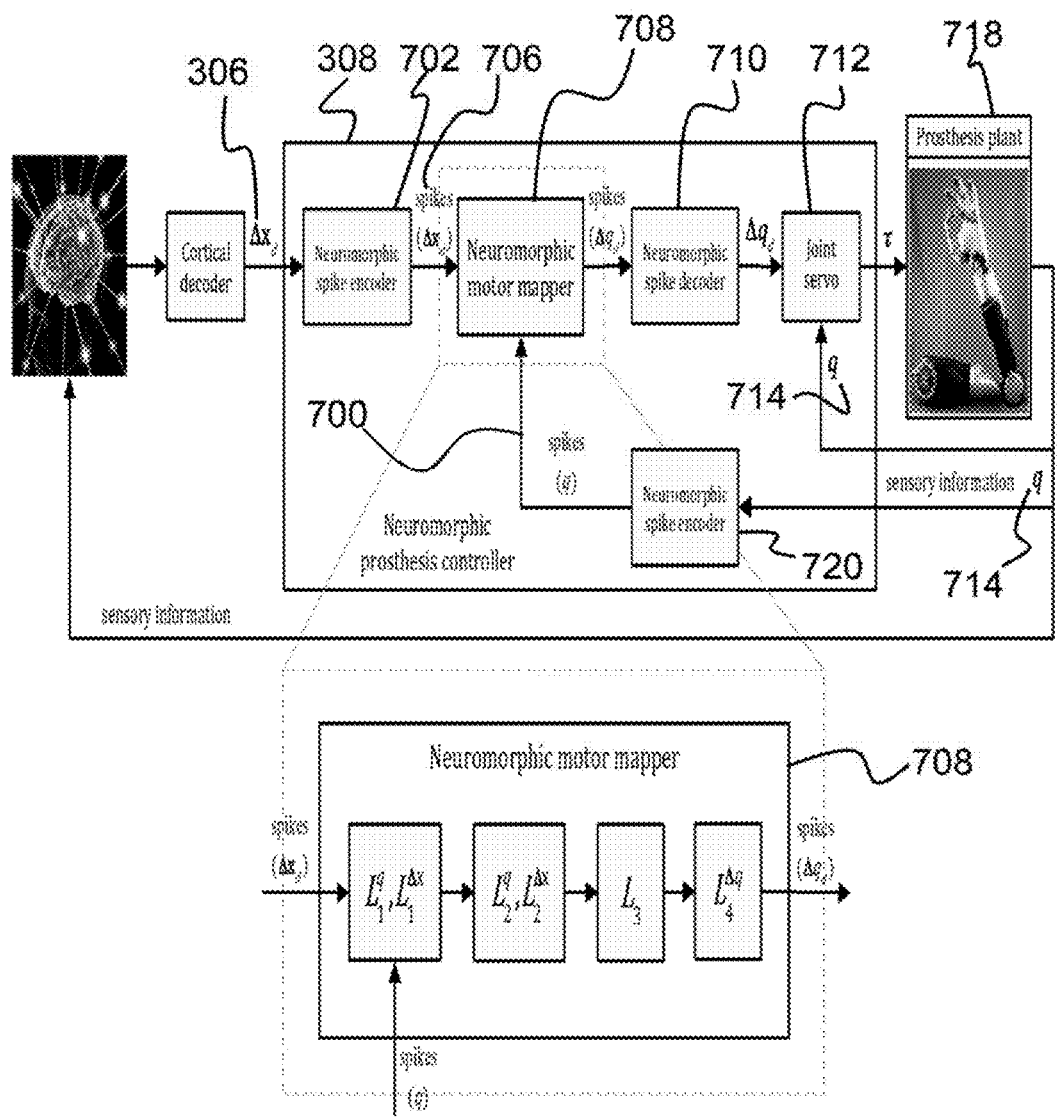
FIG. 7 is flow chart illustrating how high-level motor intent from the brain is decoded and a task-level motion command is transmitted to the prosthetic device controller.

For further understanding, FIG. 7 depicts the system-level architecture associated with the approach depicted in FIG. 6B. In this case, the prosthetic device controller (i.e., neuromorphic prosthesis controller) 308 includes a neuromorphic spike encoder 702 (to represent the motion command 306 as a set of spikes 706), a neuromorphic motor mapper 708 (as illustrated in FIGS. 6A and/or 6B) to map the neural spikes representing Cartesian displacements to neural spikes representing configuration (joint) space displacements, a spike decoder 710 (to decode the neural spikes representing configuration (joint) space displacements) and generate joint space commands, and a joint servo 712 to execute the joint space command. The sensed joint angles 714 (of the current state of the prosthetic device 718) are fed back to the joint servo 712 and to the motor mapper 708 (after spike encoding 720). Relevant physiological criteria or device power consumption criteria can be incorporated into the neuromorphic motor mapper (as illustrated in FIGS. 6A and/or 6B) to drive the postural component of motion, consistent with the conical command.

Figure 8:
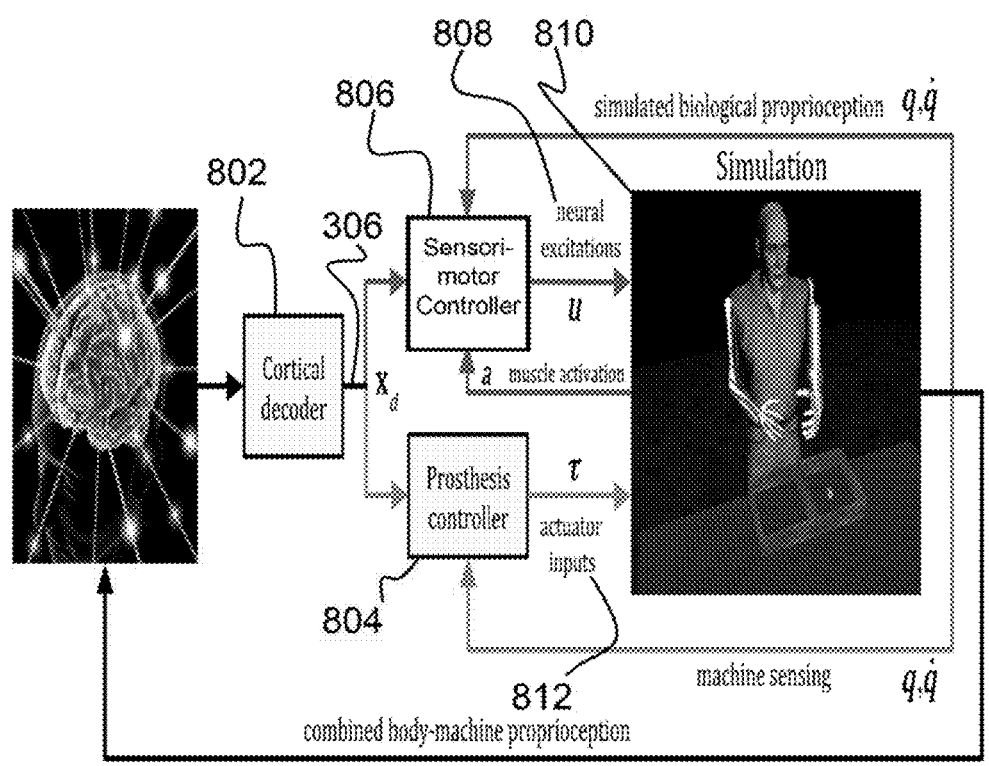
FIG. 8 is a flow chart illustrating how a decoded cortical output is sent to a simulated prosthesis controller and a simulated sensorimotor controller.

The system can also be modified to allow human-in-the-loop virtual testing of bio-integration issues associated with the prosthetic hardware. FIG. 8, for example, depicts such an architecture that includes human in-the-loop virtual testing. The decoded cortical output 306 from neuroimaging equipment 802 (e.g., EEG, fMRI, etc.) attached to the subject is sent to a simulated prosthesis controller 804 (whereas the prosthesis controller 308 in FIG. 3 is controlling an actual piece of hardware) and a simulated sensorimotor controller 806. The simulated prosthesis controller 804 models the behavior of controller designs (and operates in a manner similar to the prosthesis controller 308 described and illustrated with respect to FIG. 3), while the sensorimotor controller 806 simulates the sensorimotor processing and integration of the central nervous system (CNS).

The simulated neural excitations 808 output from this controller 806 drive a set of muscles in a musculoskeletal simulation 810, while the simulated actuator torques 812 from the prosthesis controller 804 drive the simulated prosthetic device. A single physics-based environment incorporates the musculoskeletal dynamics of the subject as well as the dynamics of the prosthetic device. This architecture allows a wealth of simulation-based testing to be performed. The overall efficacy of the prosthesis controller 804 can be tested, including stability and performance of the control system in executing cortical commands. A number of bio-integration issues can also be evaluated. These include mechanical forces and stresses on the device and the subject in various configurations, as well as reaction forces at the body-prosthetic interfaces. In addition to facilitating design optimization of the control system and prosthetic device the architecture will also facilitate subject training with the prosthetic system and subject-specific tuning and customization of the system prior to any physical coupling of the subject with the prosthetic hardware.

Figure 9:
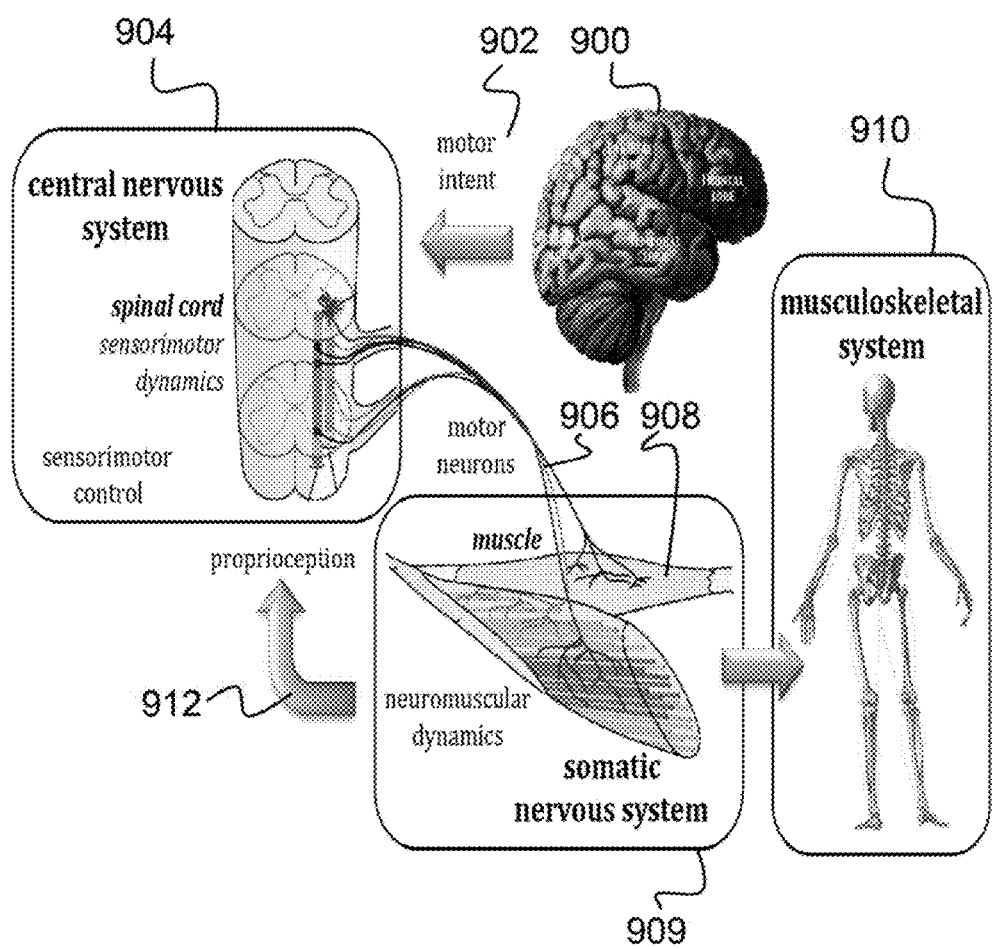
FIG. 9 is a flow chart illustrating the neural and musculoskeletal physiology associated with the motor control problem.

The sensorimotor controller 806 component is described in further detail below with respect to FIGS. 9 through 17. FIG. 9, for example, depicts the neural and musculoskeletal physiology associated with the motor control problem. High-level motor intent 900 from the brain 900 is transmitted to the central nervous system (CNS) 904. Sensorimotor integration and control results in the low-level command of motor neurons 906 innervating individual muscles 908 (in the somatic nervous system 909) to generate coordinated musculoskeletal 910 movement. Afferent proprioceptive signals 912 transmit sensory data from mechanoreceptors in the joints and tendons back to the CNS 904.

Figure 10:
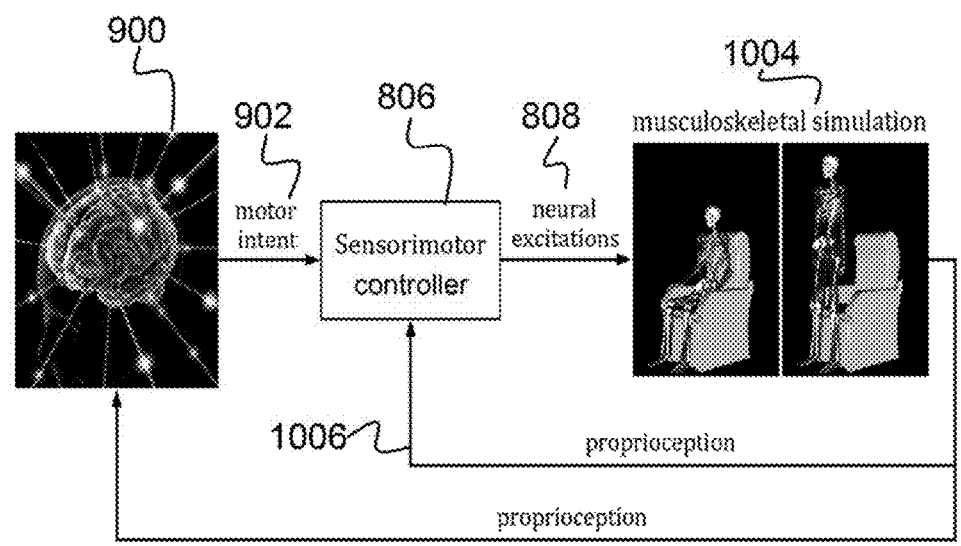
FIG. 10 is a functional block diagram depicting a system-level abstraction of FIG. 9, showing an abstracted representation of neural and musculoskeletal physiology.
Figure 13:
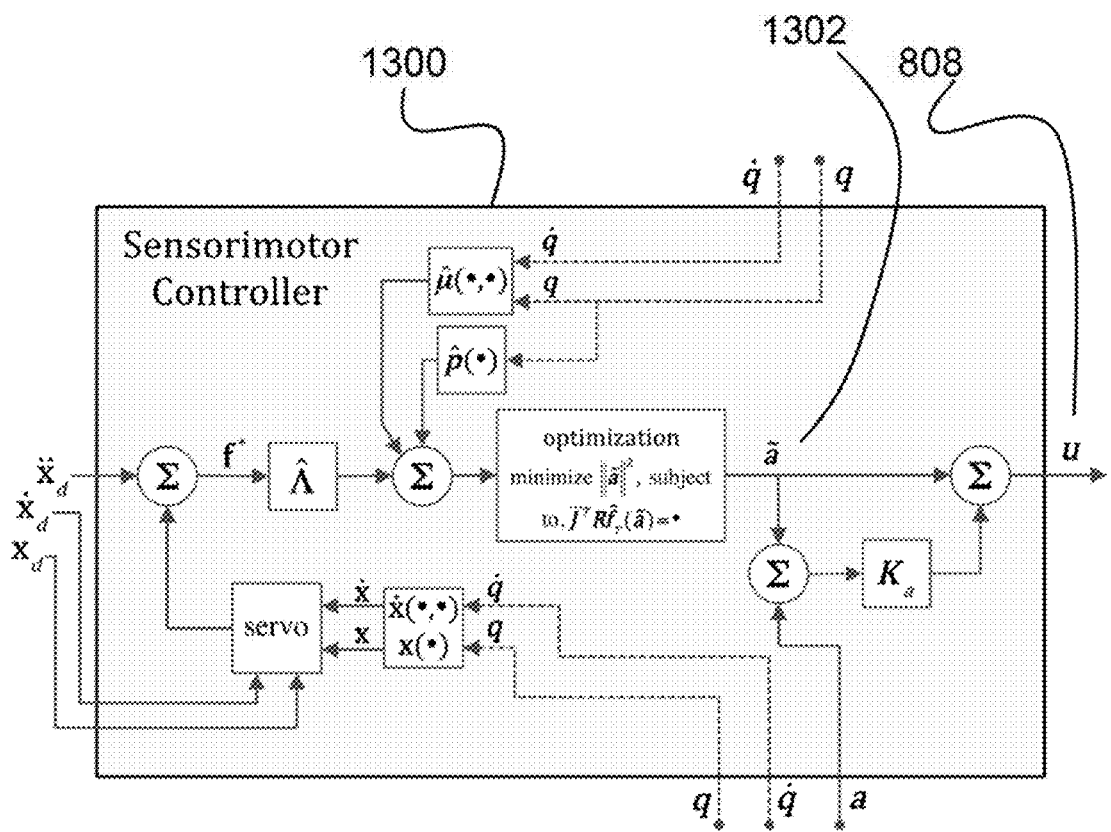
FIG. 13 is an illustration of a task-level sensorimotor controller.
Figure 16:
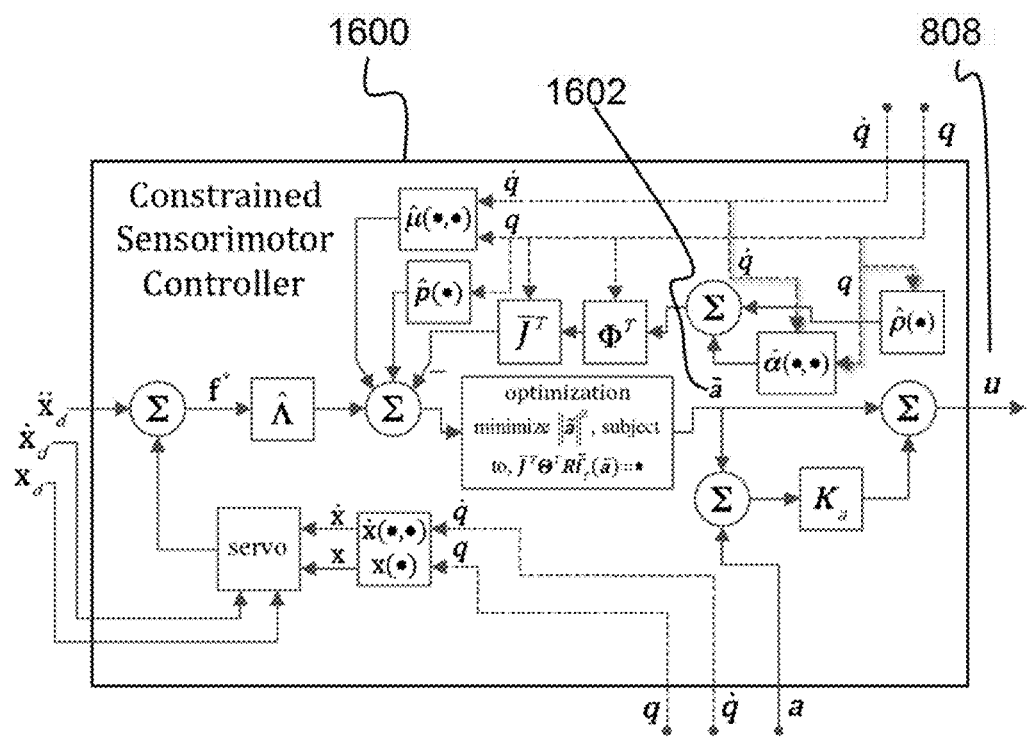
FIG. 16 is an illustration of a constrained task-level sensorimotor controller.
Figure 17:
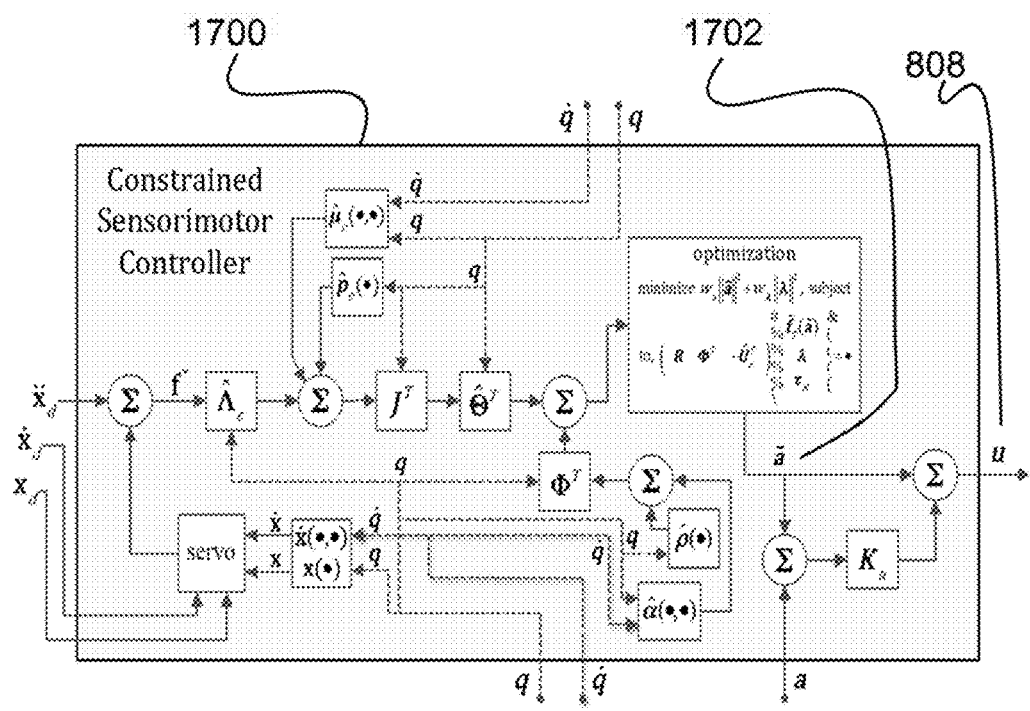
FIG. 17 is an illustration of a constrained task-level sensorimotor controller, which generates motion consistent with the input motion commands in the presence of holonomic system constraints.

FIG. 10 depicts a system-level abstraction of FIG. 9. The sensorimotor controller block 806 is central to the sensorimotor controller described herein. It receives task-level command input (i.e., motor intent 902) from the human operator (or brain 900) and generates low-level neural excitations 808 for musculoskeletal simulations 1004. This is a closed-loop control process where sensory data (via proprioceptive signals 1006) is fed back to the sensorimotor controller 806, which provides continual updates to the neural excitations 808 driving the musculoskeletal simulation 1004. Thus, in one aspect, the sensorimotor controller 806 (simulator) operates by running musculoskeletal simulations on a musculoskeletal plant. The various aspects of the sensirometor controller 806 are described in further detail below with respect to elements 1300, 1600, and 1700 as illustrated in FIGS. 13, 16, and 17, respectively.

Figure 11:
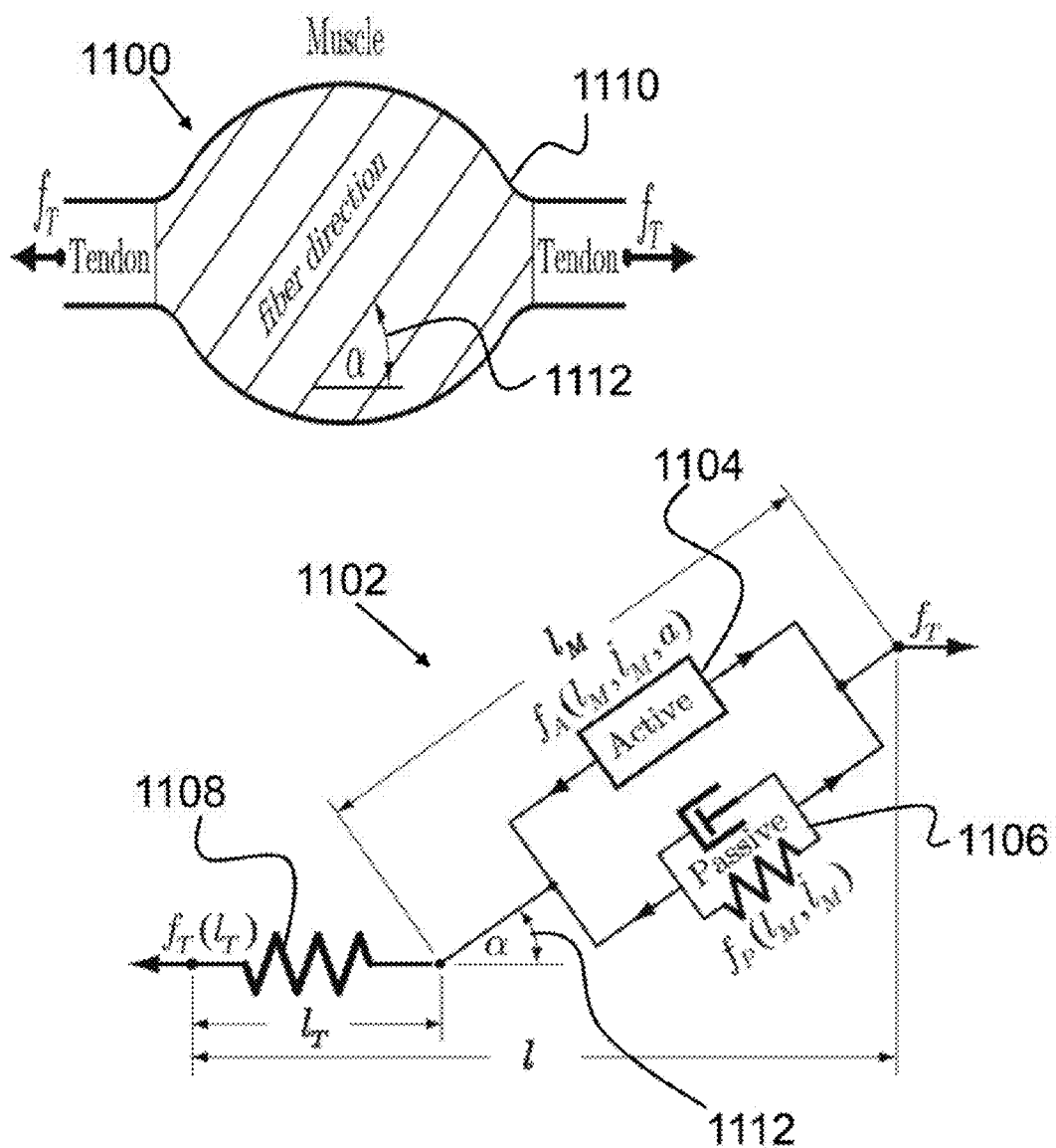
FIG. 11 is an illustration depicting an active state musculotendon model, where the active contractile element and passive viscoelastic element are in parallel and the passive elastic tendon element is in series.
Figure 12:
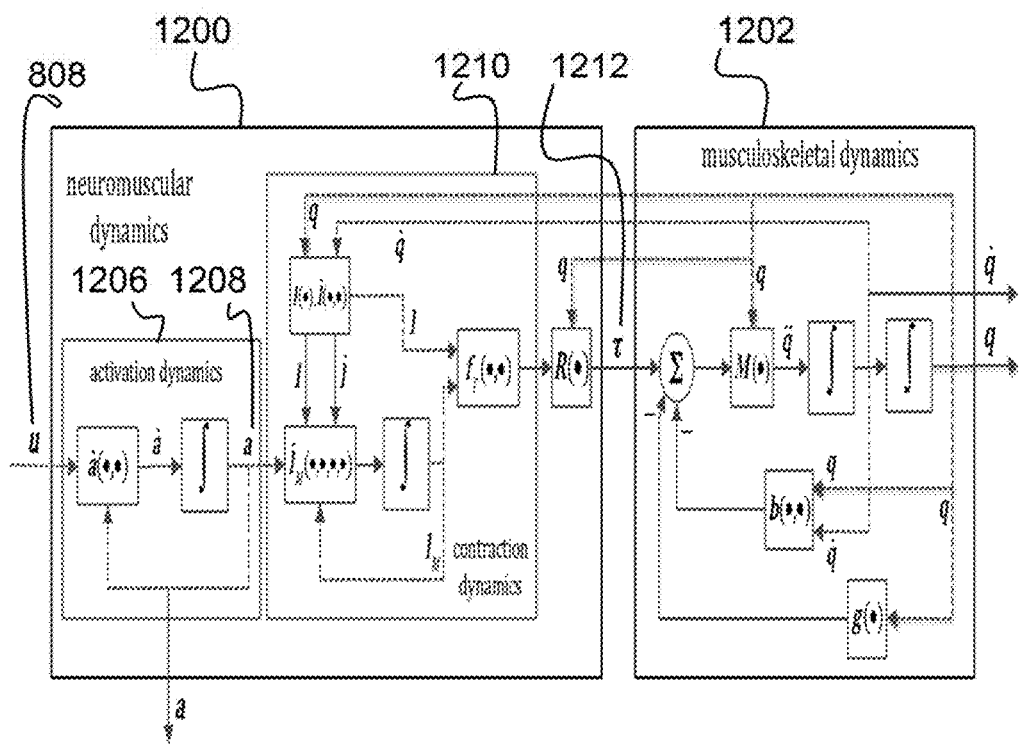
FIG. 12 is an illustration depicting a neuromuscular and musculoskeletal system (feed-forward path)

For further understanding, FIG. 11 provides an illustration of an example musculoskeletal plant 1100 according to the principles of the present invention. As shown in FIG. 12, the musculoskeletal plant can be divided in neuromuscular 1200 dynamics and musculoskeletal 1202 dynamics. Specifically, FIG. 12 is an illustration depicting a neuromuscular 1200 and musculoskeletal 1202 system (feed-forward path). As shown, neural excitations 808 provide input to the activation dynamics 1206 and output 1208 of the activation dynamics 1206 provides input to the contraction dynamics 1210. Further, output 1212 of the contraction dynamics 1210 provides input to the musculoskeletal 1202 dynamics through the joint torques.

Further details regarding the neuromuscular 1200 and musculoskeletal 1202 systems are provided below. The musculoskeletal 1202 system dynamics are described by the following system of equations in configuration space.

$$\tau = M(q)\ddot{q} + b(q,\dot{q}) + g(q),$$

where q is the vector of n generalized or joint coordinates, $\tau$, is the vector of applied joint torques, $M(q)$, is the joint space mass matrix, $b(q,\dot{q})$, is the vector of centrifugal and Coriolis forces, and $g(q)$ is the vector of gravity forces.

The neuromuscular 1202 dynamics describe the behavior of a set of r musculotendon actuators spanning the musculoskeletal system. These actuators are modeled as Hill-type active state force generating units, as described by De Sapio et al. (see Literature Reference No. 18). It is assumed that the vector of r musculotendon lengths, l, can be uniquely determined from the system configuration, q. That is, $l=l(q)$. As a consequence of this assumption, differential variations in l are given by, $$\delta l = \frac{\partial l}{\partial q} \delta q = L(q) \delta q,$$

where $L(q)$ is the muscle Jacobian. From the principle of virtual work, it is concluded that, $$\tau = -L^T f_T = R(q) f_T,$$

where $f_T$ is the vector of r tendon forces. The negative sign is due to the convention of taking contractile muscle forces as positive. The matrix of moment arms is denoted R.

The behavior of the musculotendon actuators (neuromuscular dynamics 1200) can be divided into activation dynamics 1208 and contraction dynamics 1210. Activation dynamics 1208 refers to the process of muscle activation in response to neural excitation. This process can be modeled by the following equation of state written in terms of the vector of r muscle activations, a, such that $$\dot{a} = \begin{pmatrix} \tau(u_1, a_1) & 0 & 0 \\ 0 & \ddots & 0 \\ 0 & 0 & \tau(u_r, a_r) \end{pmatrix}^{-1} (u - a),$$

where $a_i, \in [0,1]$ and $u_i [0,1]$ is the neural input. The term $\tau(u_i, a_i)$ is a time constant given by, $$\tau(u_i, a_i) = \begin{cases} (\tau_a - \tau_d)u_i + \tau_d & \text{for } u \geq a_i \\ \tau_d & \text{for } u_i < a_i \end{cases},$$

where $\tau_a$ and $\tau_d$ are the activation and deactivation time constants, respectively.

The contraction dynamics 1210 of the musculotendon unit (illustrated as element 1100 in FIG. 11) can be modeled as the lumped parameter system. Referring again to FIG. 11, the lumped parameter system 1102 describes the configuration of forces. There is an active element 1104, a passive viscoelastic element (in parallel) 1106, and an elastic tendon element (in series) 1108. The relative angle associated with the muscle fibers 1110, $\alpha$, is referred to as the pennation angle 1112.

This yields the following relations, $$l(q) = l_M \cos \alpha + l_T,$$

$$\hat{l}(q) = \hat{l}_M \cos \alpha + \hat{l}_T,$$

where $l_M$ is the vector of muscle lengths and $l_T$ is the vector of tendon lengths. The following force equilibrium equations can be expressed, $$f_T = (f_A + f_P) \cos \alpha,$$

where $f_A$ is the vector of active forces in the muscles and $f_p$ is the vector of passive forces in the muscles. Using this force equilibrium equation as well as constitutive relationships describing muscle forces as a function of muscle length and contraction velocity, $f_A(l_M, \hat{l}_M, a)$ and $f_p(l_M, \hat{l}_M)$, and tendon force as a function of tendon length, $f_T(l_T)$, the following equation of state in functional form can be expressed as, $$\hat{l}_M = \hat{l}_M(l(q), \hat{l}(q,\dot{q}), l_M, a).$$

So, for a system of r musculotendon actuators, the following system of 2r first-order state equations can be expressed as, $$\dot{a} = \dot{a}(u,a) = \begin{pmatrix} \tau(u_1,a_1) & 0 & 0 \\ 0 & \ddots & 0 \\ 0 & 0 & \tau(u_r,a_r) \end{pmatrix}^{-1} (u-a),$$

$$\hat{l}_M = \hat{l}_M(l(q), \hat{l}(q,\dot{q}), l_M, a),$$

where the internal states are $l_M$ and a. This is complemented by the force relationship, $$f_T = f_T(l_T) = l(q) - l_M \cos\alpha = f_T(l(q), l_M).$$

Returning to the musculoskeletal dynamics (depicted as element 1202 in FIG. 12), $$\tau = M(q)\ddot{q} + b(q,\dot{q}) + g(q),$$

these equations of motion can be mapped into operational or task space, as follows:

$$\bar{J}^T\tau = \bar{J}^T[M(q)\ddot{q} + b(q,\dot{q}) + g(q)] \rightarrow$$
$$\bar{J}^T\tau = f = \Lambda(q)\ddot{x} + \mu(q,\dot{q}) + p(q),$$

where $\bar{J}$ is the dynamically consistent inverse of the task Jacobian, x is a description of task coordinates that are to be controlled, f, are the control forces that act at the task, and $\Lambda(q)$, $\mu(q,\dot{q})$, and $p(q)$, are the task space mass matrix, centrifugal and Coriolis force vector, and gravity force vector, respectively. See the work of Khatib in Literature Reference No. 10 for a discussion of task space, which is hereby incorporated by reference as through fully set forth herein.

Given a system of r musculotendon actuators, the applied joint torques are given by, $$\tau = Rf_\tau,$$

which provides the following muscle actuated task space equations of motion, $$\bar{J}^T Rf_\tau = \Lambda\ddot{x} + \mu + p.$$

For control purposes, the muscle actuated task space equations of motion can be expressed as:

$$\bar{J}^T Rf_T = \hat{\Lambda}f^* + \hat{\mu} + \hat{p}.$$

where $\hat{\cdot}$ represents estimates of the dynamic parameters and $f^*$ is the control law. Since the term $\bar{J}^T Rf_T$ is underdetermined it offers many solutions for $f_T$. These solutions correspond to the kinematic redundancy associated with the task and the actuator redundancy associated with the system of musculotendon force actuators. In the computed muscle control approach of Thelen et al., (see Literature Reference Nos. 19 and 20), there was only muscle redundancy that needed to be resolved. This was achieved through a static optimization step. In the task-level formulation as used herein, a static optimization is also specified to resolve both muscle redundancy and kinematic redundancy. Specifically, a set of muscle activations, ã, is determined, which minimizes $\|\tilde{a}\|^2$, where ã are muscle activations associated with the steady state tendon forces $\hat{f}_T(\tilde{a})$ (i.e., tendon forces at a time when the contraction dynamics have equilibrated and the transients have decayed). Further these activations must generate steady state tendon forces that satisfy the task motion requirements, $$\bar{J}^T R\hat{f}_T(\tilde{a}) = \hat{\Lambda}f^* + \hat{\mu} + \hat{p}.$$

Using a linear proportional controller, a set of neural excitations, u, is computed which causes the actual activations, α, from the forward neuromuscular simulation to track ã, as follows:

$$u = \tilde{a} + K_a(\tilde{a} - a),$$

where $K_a$ is the gain. This task-level input computed muscle control architecture is depicted in FIG. 13. FIG. 13 is an illustration of a task-level sensorimotor controller 1300 according to the principles of the present invention, where motion commands are represented in task space. The sensorimotor controller 1300 generates optimal neural excitation commands 808 that minimize muscle activation 1302, and generate motion consistent with the input motion commands.

Figure 14:
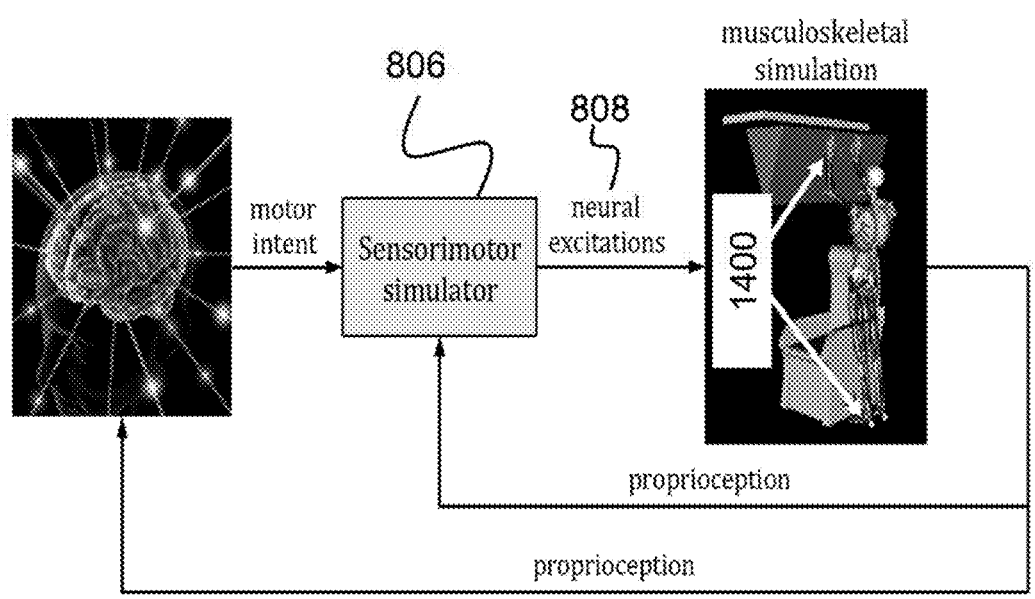
FIG. 14 is a functional block diagram depicting an abstracted representation of neural and musculoskeletal physiology.

Further and as shown in FIG. 14, holonomic constraints 1400 can be incorporated into the system. Specifically, FIG. 14 illustrates a functional block diagram showing an abstracted representation of neural and musculoskeletal physiology. The sensorimotor controller 806 in this aspect is a goal-oriented neuromuscular feedback controller that drives the constrained 1400 musculoskeletal simulation by specifying low-level neural 808 excitations that execute task-level commands.

Figure 15:
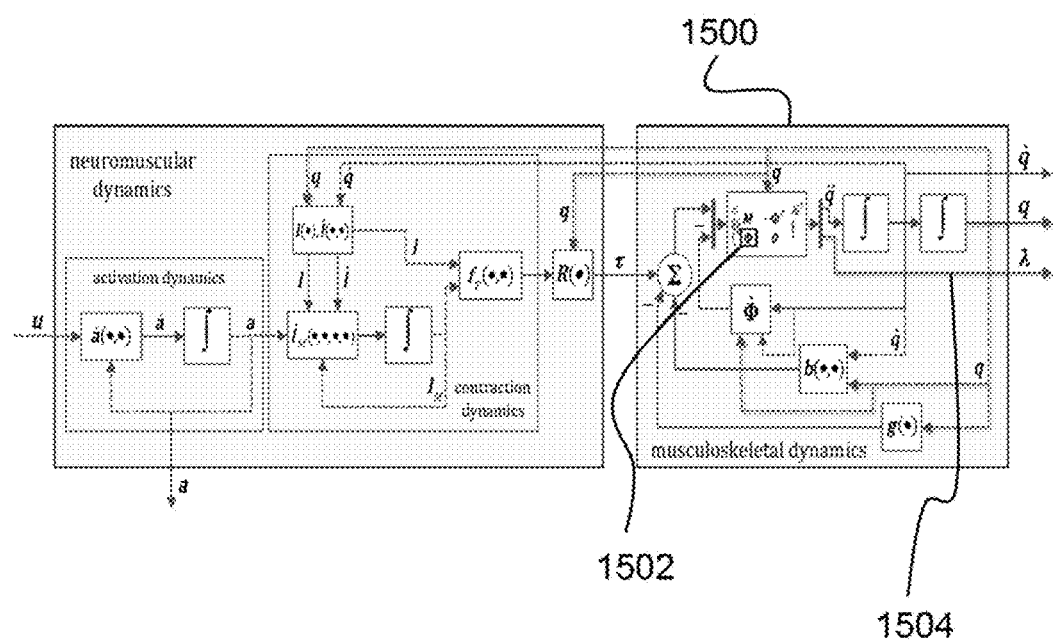
FIG. 15 is an illustration depicting a neuromuscular and musculoskeletal system (feed-forward path), showing the musculoskeletal system dynamics augmented with a set of holonomic constraints and Lagrange multipliers.

Thus and as shown in FIG. 15, the holonomic constraints, $\phi(q)=0$, can be incorporated into the musculoskeletal dynamics. The configuration space dynamics was augmented with Lagrange multipliers, λ, $$\tau = M(q)\ddot{q} + b(q,\dot{q}) + g(q) - \Phi^T\lambda,$$

where $\Phi^T$ is the constraint Jacobian. The block diagram of the constrained musculoskeletal system is depicted in FIG. 15. Specifically, FIG. 15 is an illustration depicting a neuromuscular and constrained musculoskeletal system (feedforward path), showing the musculoskeletal system dynamics 1500 augmented with a set of holonomic constraints 1502 and Lagrange multipliers 1504.

The approach expresses these dynamics in one of two ways. First and as shown in FIG. 16, the constrained dynamics can be represented in task space as:

$$\bar{J}^T\Theta^T\tau = \Lambda(q)\ddot{x} + \mu(q,\dot{q}) + p(q) - \bar{J}^T\Phi^T(\alpha + \rho),$$

where $\Theta^T$ is the constraint null space projection matrix. Task space representations were described by De Sapio et al. in Literature Reference No. 21. The centrifugal and Coriolis forces, and gravity forces projected at the constraints are α and ρ respectively. For neuromuscular control purposes, this can be expressed as the following muscle actuated task space equations of motion, $$\bar{J}^T\Theta^T Rf_T = \hat{\Lambda}f^* + \hat{\mu} + \hat{p} - \bar{J}^T\Phi^T(\hat{\alpha} + \hat{\rho}).$$

As before, the controller 1600 seeks a 1602, which minimizes $\|\tilde{a}\|^2$ (i.e., magnitude squared of the activations) to generate the neural excitations 808. Further these activations must generate steady state tendon forces that satisfy the constrained task motion requirements, as follows:

$$\bar{J}^T\Theta^T R\hat{f}_T(\tilde{a}) = \hat{\Lambda}f^* + \hat{\mu} + \hat{p} - \bar{J}^T\Phi^T(\hat{\alpha} + \hat{\rho}).$$

Alternately and as shown in FIG. 17, constrained dynamics can be represented in task space as $$\tau = \Theta^T J^T(\Lambda_c\ddot{x} + \mu_c + p_c) + \Phi^T(\alpha + \rho) + U_c^T\tau_N - \Phi^T\lambda,$$

where $\Theta^T$ is the constraint null space projection matrix, $\Lambda_c, \mu_c, p_c$, are the task/constraint space mass matrix, centrifugal and Coriolis force vector, and gravity force vector, respectively. Task space representations were further described in Literature Reference Nos. 16 and 17. The centrifugal and Coriolis forces, and gravity forces projected at the constraints are α and ρ respectively. Finally, $U_c^T$ is the combined null space projection matrix, with respect to both task and constraints, and $\tau_N$ is the control vector for the null space.

This representation exposes the constraint forces and is useful for generating optimal neural excitations that track task motion under constraints and also minimizes specific internal joint reaction forces. For neuromuscular control purposes, this can be expressed as the following muscle actuated task space equations of motion, $$Rf_T + \Phi^T\lambda - \hat{U}_c^T\tau_N = \Theta^T J^T(\hat{\Lambda}_c f^* + \hat{\mu}_c + \hat{p}_c) + \Phi^T(\hat{\alpha} + \hat{p}).$$

Thus, the system now seeks $\tilde{\alpha}$ and $\lambda$, which minimize $w_\alpha\|\tilde{\alpha}\|^2 + w_\lambda\|\lambda\|^2$. Further these activations must generate steady state tendon forces that satisfy the constrained task motion requirements, $$\begin{pmatrix} R & \Phi^T & -\hat{U}_c^T \end{pmatrix} \begin{pmatrix} \tilde{f}_T(\tilde{a}) \\ \lambda \\ \tau_N \end{pmatrix} = \Theta^T J^T(\hat{\Lambda}_c f^* + \hat{\mu}_c + \hat{p}_c) + \Phi^T(\hat{\alpha} + \hat{p}).$$

Thus, FIG. 17 is an illustration of a constrained task-level sensorimotor controller 1700 based on a reformulation of the computed muscle control approach. The system represents motion commands in task space and generates optimal neural excitation 808 commands that minimize muscle activation 1702, and generates motion consistent with the input motion commands in the presence of holonomic system constraints.

What is claimed is:

1. A system for controlling a torque controlled prosthetic device given motor intent inferred from neuroimaging data, the system comprising:
   one or more processors and a memory, the memory having executable instructions encoded thereon, such that upon execution of the instructions, the one or more processors perform operations of:
      receiving neuroimaging data of a user from a neuroimaging device;
      decoding the neuroimaging data to infer spatial motion intent of the user, where the spatial motion intent includes desired motion commands of the torque controlled prosthetic device represented in a coordinate system;
      executing, with a prosthesis controller, the motion commands as torque commands to cause the torque controlled prosthetic device to move according to the spatial motion intent of the user;
   wherein the prosthesis controller is a neuromorphic prosthesis controller and further comprises:
      a neuromorphic spike encoder to represent the motion command as a set of neural spikes;
      a neuromorphic motor mapper to map the neural spikes representing Cartesian displacements to neural spikes representing configuration (joint) space displacements;
      a spike decoder to decode the neural spikes representing configuration (joint) space displacements and generate a joint space command; and
      a joint servo to execute the joint space command.

2. The system as set forth in claim 1, further comprising at least one torque controlled prosthetic device operably connected with the one or more processors.

3. The system as set forth in claim 2, further comprising an operation of receiving, in the controller, sensory information regarding a current state of the prosthetic device.

4. The system as set forth in claim 3, wherein in executing the motion commands, the motion commands are executed using a task decomposition and posture decomposition, wherein the task decomposition is a task space control and the posture decomposition is formulated as a cost potential which represents a cost function.

5. The system as set forth in claim 4, wherein in executing the motion commands, the motion commands are executed as torque commands that generate a desired task space control while minimizing the cost potential.

6. The system as set forth in claim 3, wherein in executing the motion commands, the motion commands are executing using a spiking neural network.

7. A system for controlling a torque controlled prosthetic device given motor intent inferred from neuroimaging data, the system comprising:
   one or more processors and a memory, the memory having executable instructions encoded thereon, such that upon execution of the instructions, the one or more processors perform operations of:
      receiving neuroimaging data of a user from a neuroimaging device;
      decoding the neuroimaging data to infer spatial motion intent of the user, where the spatial motion intent includes desired motion commands of the torque controlled prosthetic device represented in a coordinate system;
      executing, with a prosthesis controller, the motion commands as torque commands to cause the torque controlled prosthetic device to move according to the spatial motion intent of the user;
      receiving a model of the prosthetic device and a musculoskeletal model of the user, wherein the musculoskeletal model includes musculoskeletal dynamics that include steady state tendon forces;
      generating, with a sensorimotor controller, simulated neural excitations given the motion commands to drive a set of muscle activations in a musculoskeletal simulation; and
      generating, with the prosthesis controller, simulated actuator joint torques given the motion commands to drive a simulated prosthetic device.

8. A computer program product for controlling a torque controlled prosthetic device given motor intent inferred from neuroimaging data, the computer program product comprising:
   a non-transitory computer-readable medium having executable instructions encoded thereon, such that upon execution of the instructions by one or more processors, the one or more processors perform operations of:
      receiving neuroimaging data of a user from a neuroimaging device;
      decoding the neuroimaging data to infer spatial motion intent of the user, where the spatial motion intent includes desired motion commands of the torque controlled prosthetic device represented in a coordinate system;
      executing, with a prosthesis controller, the motion commands as torque commands to cause the torque controlled prosthetic device to move according to the spatial motion intent of the user;
   wherein the prosthesis controller is a neuromorphic prosthesis controller and further comprises:

a neuromorphic spike encoder to represent the motion command as a set of neural spikes;
a neuromorphic motor mapper to map the neural spikes representing Cartesian displacements to neural spikes representing configuration (joint) space displacements;
a spike decoder to decode the neural spikes representing configuration (joint) space displacements and generate a joint space command; and
a joint servo to execute the joint space command.

9. The computer program product as set forth in claim 8, further comprising instructions for controlling at least one torque controlled prosthetic device that is operably connected with the one or more processors.

10. The computer program product as set forth in claim 9, further comprising an operation of receiving, in the controller, sensory information regarding a current state of the prosthetic device.

11. The computer program product as set forth in claim 10, wherein in executing the motion commands, the motion commands are executed using a task decomposition and posture decomposition, wherein the task decomposition is a task space control and the posture decomposition is formulated as a cost potential which represents a cost function.

12. The computer program product as set forth in claim 11, wherein in executing the motion commands, the motion commands are executed as torque commands that generate a desired task space control while minimizing the cost potential.

13. The computer program product as set forth in claim 10, wherein in executing the motion commands, the motion commands are executing using a spiking neural network.

14. A computer program product for controlling a torque controlled prosthetic device given motor intent inferred from neuroimaging data, the computer program product comprising:
a non-transitory computer-readable medium having executable instructions encoded thereon, such that upon execution of the instructions by one or more processors, the one or more processors perform operations of:
receiving neuroimaging data of a user from a neuroimaging device;
decoding the neuroimaging data to infer spatial motion intent of the user, where the spatial motion intent includes desired motion commands of the torque controlled prosthetic device represented in a coordinate system;
executing, with a prosthesis controller, the motion commands as torque commands to cause the torque controlled prosthetic device to move according to the spatial motion intent of the user;
receiving a model of the prosthetic device and a musculoskeletal model of the user, wherein the musculoskeletal model includes musculoskeletal dynamics that include steady state tendon forces;
generating, with a sensorimotor controller, simulated neural excitations given the motion commands to drive a set of muscle activations in a musculoskeletal simulation; and
generating, with the prosthesis controller, simulated actuator joint torques given the motion commands to drive a simulated prosthetic device.

15. A method for controlling a torque controlled prosthetic device given motor intent inferred from neuroimaging data, the method comprising an act of
executing instructions encoded on a memory, such that upon execution of the instructions, one or more processors perform operations of:
receiving neuroimaging data of a user from a neuroimaging device;
decoding the neuroimaging data to infer spatial motion intent of the user, where the spatial motion intent includes desired motion commands of the torque controlled prosthetic device represented in a coordinate system; and
executing, with a prosthesis controller, the motion commands as torque commands to cause the torque controlled prosthetic device to move according to the spatial motion intent of the user, wherein the prosthesis controller is a neuromorphic prosthesis controller and further comprises:
a neuromorphic spike encoder to represent the motion command as a set of neural spikes;
a neuromorphic motor mapper to map the neural spikes representing Cartesian displacements to neural spikes representing configuration (joint) space displacements;
a spike decoder to decode the neural spikes representing configuration (joint) space displacements and generate a joint space command; and
a joint servo to execute the joint space command.

16. The method as set forth in claim 15, further comprising an act of controlling at least one torque controlled prosthetic device that is operably connected with the one or more processors.

17. The method as set forth in claim 16, further comprising an operation of receiving, in the controller, sensory information regarding a current state of the prosthetic device.

18. The method as set forth in claim 17, wherein in executing the motion commands, the motion commands are executed using a task decomposition and posture decomposition, wherein the task decomposition is a task space control and the posture decomposition is formulated as a cost potential which represents a cost function.

19. The method as set forth in claim 18, wherein in executing the motion commands, the motion commands are executed as torque commands that generate a desired task space control while minimizing the cost potential.

20. The method as set forth in claim 17, wherein in executing the motion commands, the motion commands are executing using a spiking neural network.

21. A method for controlling a torque controlled prosthetic device given motor intent inferred from neuroimaging data, the method comprising an act of
executing instructions encoded on a memory, such that upon execution of the instructions, one or more processors perform operations of:
receiving neuroimaging data of a user from a neuroimaging device;
decoding the neuroimaging data to infer spatial motion intent of the user, where the spatial motion intent includes desired motion commands of the torque controlled prosthetic device represented in a coordinate system;
executing, with a prosthesis controller, the motion commands as torque commands to cause the torque controlled prosthetic device to move according to the spatial motion intent of the user;
receiving a model of the prosthetic device and a musculoskeletal model of the user, wherein the musculoskeletal model includes musculoskeletal dynamics that include steady state tendon forces;

generating, with a sensorimotor controller, simulated neural excitations given the motion commands to drive a set of muscle activations in a musculoskeletal simulation; and generating, with the prosthesis controller, simulated actuator joint torques given the motion commands to drive a simulated prosthetic device.

* * * * *